United States Patent
Kaspar et al.

(10) Patent No.: US 7,101,540 B2
(45) Date of Patent: *Sep. 5, 2006

(54) TARGETED RETROGRADE GENE DELIVERY TO MOTOR NEURONS

(75) Inventors: Brian K. Kaspar, San Diego, CA (US); Fred H. Gage, La Jolla, CA (US)

(73) Assignee: The Salk Institute For Biological Studies, La Jolla, CA (US)

( * ) Notice: Subject to any disclaimer, the term of this patent is extended or adjusted under 35 U.S.C. 154(b) by 227 days.

This patent is subject to a terminal disclaimer.

(21) Appl. No.: 10/237,567

(22) Filed: Sep. 5, 2002

(65) Prior Publication Data

US 2003/0118556 A1 Jun. 26, 2003

Related U.S. Application Data

(63) Continuation-in-part of application No. 10/032,047, filed on Dec. 21, 2001.

(51) Int. Cl.
*A61K 48/00* (2006.01)
*C12N 15/864* (2006.01)

(52) U.S. Cl. .................. 424/93.2; 435/320.1; 435/456; 514/44

(58) Field of Classification Search ............... 424/93.2; 514/44; 435/320.1, 456
See application file for complete search history.

(56) References Cited

U.S. PATENT DOCUMENTS

| 4,955,892 | A | 9/1990 | Daniloff |
| 5,092,871 | A | 3/1992 | Aebischer et al. |
| 6,632,427 | B1 | 10/2003 | Finiels et al. |
| 2002/0031493 | A1 | 3/2002 | Horellou et al. |
| 2003/0050273 | A1 | 3/2003 | Ozawa et al. |
| 2003/0118552 | A1 * | 6/2003 | Kaspar et al. ............. 424/93.2 |

FOREIGN PATENT DOCUMENTS

WO WO 200142481 A2 * 6/2001

OTHER PUBLICATIONS

Baumgartner et al., "Neuroprotection of spinal motorneurons following targeted transduction with an adenoviral vector carrying the gene for glial cell line-derived neurotrophic factor," Exp. Neurol. 153(1): 102-112, Sep. 1998).*
Yamashita et al., "Bcl-2 expression by retrograde transport of adenoviral vecotrs with Cre-IoxP recombination system in motor neurons of mutant SOD1 transgenic mice," Gene Ther. 8(13): 977-986, Jul. 2001.*
Yamashita et al., "Effect on motor neuron survival in mutant SOD1 (G93A) transgenic mice by Bcl-2 expression using retrograde axonal transport of adenoviral vectors," Neurosci. Lett. 328(3): 289-293, Aug. 16, 2002.*
Wang et al., "Neuroprotective effect of glial cell line-derived neurotrophic neurotrophic factor mediated by an adeno-associated virus in a transgenic animal model of amyotrophic lateral sclerosis," J. Neurosci. 22(16): 6920-6928, Aug. 15, 2002.*
Kaspar et al., "Targeted retrograde gene delivery for neuronal protection," Mol. Ther. 5(1): 50-56, Jan. 2002.*
Aebischer & Ridet, Recombinant Proteins for Neurodegenerative Diseases: The Delivery Issue, Trends Neurosciences, 2001 24(9):533-40.
Antonawich et al., BCL-2 Transduction, Using a Herpes Simplex Virus Amplicon, Protects Hippocampal Neurons from Transient Global Ischemia, Academic Press, Experimental Neurology 156, 130-137 (1999).
Bartlett et al., Infectious Entry Pathway of Adeno-Associated Virus and Adeno-Associated Virus Vectors, Journal of Virology, Mar. 2000, p. 2777-2785.
Bartlett et al., Selective and Rapid Uptake of Adeno-Associated Virus Type 2 in Brain, Human Gene Therapy 9:1181-1186 (May 20, 1998).
Blomer et al., BCL-XL Protects Adult Septal Cholinergic Neurons from Axotomized Cell Death, Proc. Natl. Acad. Sci. USA vol. 95, pp. 2603-2608, Mar. 1998.
Calamandrei and Alleva, Neuronal Growth Factors, Neurotrophins and Memory Deficiency, Behav Brain Res 1995 Jan. 23;66(1-2):129-32.
Carver and Barness, Trophic Factors for the Gastrointestinal Tract, Clin Perinatol (1996) 23(2):265-85.
Cleveland et al., From Charcot to SOD1: Mechanisms of Selective Motor Neuron Death in ALS, Neuron, vol. 24, 515-520, Nov. 1999.
DeFalco et al., Virus-Assisted Mapping of Neural Inputs to a Feeding Center in the Hypothalamus, *Science* 291:2608-2613 (Mar. 2001).
Dolorfo & Amaral, Entorhinal Cortex of the Rat: Topographic Organization of the Cells of Origin of the Perforant Path Projection to the Dentate Gyrus, The Journal of Comparative Neurology 398:25-48 (1998).
Duvoisin, Roger C., Overview of Parkinson's Disease, Annals New York Academy of Sciences, pp. 187-193.

(Continued)

Primary Examiner—Scott D. Priebe
(74) Attorney, Agent, or Firm—Klarquist Sparkman, LLP

(57) ABSTRACT

Methods are disclosed for delivering a heterologous gene to a cell body of a neuron by contacting a muscle tissue innervated by the neuron with a viral vector comprising a heterologous gene, wherein the viral vector enters said neuron and is retrogradely moved to the cell body. Additionally, methods for expressing secreted proteins from a nerve cell body as well as methods for treating neurodegenerative disorders such as amyotrophic lateral sclerosis are described.

13 Claims, 9 Drawing Sheets

OTHER PUBLICATIONS

Fawcett J.W., Spinal Cord repair: From Experimental Models to Human Application, Spinal Cord (1998) 36(12):811-7.

Gomez-Isla et al., Profound Loss of Layer II Entorhinal Cortex Neurons Occurs in Very Mild Alzheimer's Disease, The Journal of Neuroscience, Jul. 15, 1996, 16(14):4491-4500.

Gonzalez-Garcia, BXL-X is Expressed in Embryonic and Postnatal Neural Tissues and Functions to Prevent Neuronal Cell Death, Proc. Natl. Acad. Sci, USA, vol. 92, pp. 4304-4308, May 1995.

Hefti et al., Development of Neurotrophic Factor Therapy for Alzheimer's Disease, Ciba Found Symp. (1996)196:54-69.

Kaplitt, et al., Long-Term Gene Expression and Phenotypic Correction Using Adeno-Associated Virus Vectors in the Mammalian Brain, Nature Genetics, vol. 8, Oct. 1994.

Kishi & Cowan, A Quantitative EM Autoradiographic Study of the Commissural and Associational Connections of the Dentate Gyrus in the Rat, Anat. Embryol. 160, 173-186 (1980).

Koliatsos V.E., Biological Therapies for Alzheimer's Disease: Focus on Trophic Factors, Crit Rev Neurobiol (1996) 10(2):205-38.

Latchman & Coffin, Viral Vectors for Gene Therapy in Parkinson's Disease, Rev Neurosci. (2001) 12(1):69-78.

Monahan & Samulski, AAV Vectors: is Clinical Success on the Horizon?, Gene Therapy (2000) 7, 24-30.

Monahan & Samulski, Adeno-Associated Virus Vectors for Gene Therapy: More Pros than Cons?, Mol Med Today. (2000) 6(11):433-40.

Offen et al., Apoptosis as a General Cell Death Pathway in Neurodegenerative Diseases, J Neural Transm Suppl. (2000) 58:153-66.

Peterson et al., Central Neuronal Loss and Behavioral Impairment in Mice Lacking Neurotrophin Receptor p. 75, The Journal of Comparative Neurology 404:1-20 (1999).

Qing et al., Human Fibroblast Growth Factor Receptor 1 is a Co-Receptor for Infection by Adeno-Associated Virus 2 Nature Medicine, vol. 5, No. 1, pp. 71-77, Jan. 1999.

Senut et. al., Intraneuronal Aggregate Formation and Cell Death after Viral Expression of Expanded Polyglutamine Tracts in the Adult Rat Brain, J Neurosci. 2000 Jan. 1; 0(1):219-229.

Smith-Arica & Bartlett, Gene Therapy: Recombinant Adeno-Associated Virus Vectors, Curr Cardiol Rep. (2001) 3(1):43-9.

Snyder, et al. Effective and Stable Adeno-Associated Virus-Mediated Transduction in the Skeletal Muscle of Adult Immunocompetent Mice, Hum Gene Ther. Nov. 1, 1997 8(16):1891-900.

Summerford et al., $\alpha V\beta 5$ Integrin: a Co-Receptor for Adeno-Associated Virus Type 2 Infection, Nature Medicine, vol. 5, No. 1, pp. 78-82, Jan. 1999.

Terenghi G., Peripheral Nerve Regeneration and Neurotrophic Factors, J Anat (1999) 194 (Pt 1):1-14.

Yamada et al., Herpes Simplex Virus Vector-Mediated Expression of BCL-2 Prevents 6-Hydroxydopamine-Induced Degeneration of Neurons in the Substantia Nigra in Vivo, Proc. Natl. Acad. Sci., vol. 96, pp. 4078-4083, Mar. 1999.

Yuen EC, The Role of Neurothrophic Factors in Disorders of Peripheral Nerves and Motor Neurons, Phys Med Rehabil Clin N Am. (2001) 12(2):293-306, viii.

Yuen et al., Therapeutic Potential of Neurotrophic Factors for Neurological Disorders, Am. Neurol. (1996) 40(3):346-54.

Xiao et al., Production of High-Titer Recombinant Adeno-Associated Virus Vectors in the Absence of Helper Adenovirus, Journal of Virology, Mar. 1998, p. 2224-2232.

Xiao et al., Gene Transfer by Adeno-Associated Virus Vectors into the Central Nervous System, Experimental Neurology 144, 113-124 (1997).

Gurney et al., Motor Neuron Degeneration in Mice That Express a Human Cu,Xn Superoxide Dismutase Mutation, Science, vol. 264, p. 1772-1775, Jun. 17, 1994.

Peel et al., Adeno-Associated Virus Vectors: Activity and Applications in the CNS, Journal Neuroscience Methods 98 (2000) 95-104.

Dorland's Illustrated Medical Dictionary, $28_{th}$ Edition, W.B. Saunders Co., Philadelphia, PA, 1994, pp. 832, 1131, 1361.

Hsich et al., "critical issues in gene therapy for neurologic disease," Human Gene Therapy 13:579-604, Mar. 20, 2002.

Orkin et al., Report and Recommendations of the Panel to Asses the NIH Investment in Research on Gene Therapy, Issued Dec. 7, 1995 by the US National Inst. Of Health, Bethesda, MD.

Peterson et al., "Prophylactic neuroprotection of injured entorhinal cortical neurons by retrograde in vivo gene delivery of an anti-apoptotic transgene," European Journal of Neuroscience 12 (Suppl. 11): 233, Abstract 110.13, Jun. 2000.

Rosenberg et al., "Gene therapist, heal thyself," Science 287: 1751, Mar. 10, 2000.

Simon et al., "bcl-2 gene therapy exacerbates excitotoxicity," Human Gene Therapy 10:1715-1720, Jul. 1, 1999.

Verma et al., "Gene therapy—promises, problems and prospects," Nature 389:239-242, Sep. 18, 1997.

Mellecamps, S. et al., Synaptic Sprouting Increases the Uptake Capacities of Motoneurons In Amyotrophic Lateral Sclerosis Mice. Proced. Nat. Acad. Sci. Jun. 19, 2001, vol. 98, No. 13, pp. 7582-7587.

Chamberlin, N. L. et al. Recombinant Adeno-Associated Virus Vector: Use for Transgene Expression and Anterograde Tract Tracing in the CNS. Brain Research. 1998, vol. 793, pp. 169-175.

Bjorklund, A. et al. Towards a Neuroprotective Gene Therapy for Parkinson's disease: Use of Adenovirus, AAV and Lentivirus Vectors for Gene Transfer of GDNF to the Nigrostriatal System in the Rat Parkinson Model. Brain Research. 2000, vol. 886, pp. 82-98.

Kaplitt, M. G. et al. Long-Term Gene Expression and Phenotypic Correction Using Adeno-Associated Virus Vectors in the Mammalian Brain. Nature Genetics. Oct. 1994, vol. 8, pp. 148-154.

Skorupa, A. F. et al. Sustainded Production of Beta-Glucuronidase from Localized Sites After AAV Vector Gene Transfer Results in Widespread Distribution of Enzyme and Reversal of Lysomal Storage Lesions in a Large Volume of Brain in Mucopolysaccharidosis VII Mice. Experimental Neurology. 1999, vol. 160, pp. 17-27.

Baumgartner et al., "Targeted Transduction of CNS Neurons with Adenoviral Vectors Carrying Neurotrophic Factor Genes Confers Neuroprotection that Exceeds the Transduced Population," The Journal of Neuroscience 17(17):6504-6511, 1997.

Bordet et al., "Protective effects of cardiotrophin-1 adenoviral gene transfer on neuromuscular degeneration in transgenic ALS mice," Human Molecular Genetics 10(18):1925-1933, 2001.

Kaspar et al., "Retrograde Viral Delivery of IGF-1 Prolongs Survival in a Mouse ALS Model," Science 301:839-842, 2003.

Soudais et al., "Preferential transduction of neurons by canine adenovirus vectors and their efficient retrograde transport in vivo," The FASEB Journal 15:2283-2285, 2001.

* cited by examiner

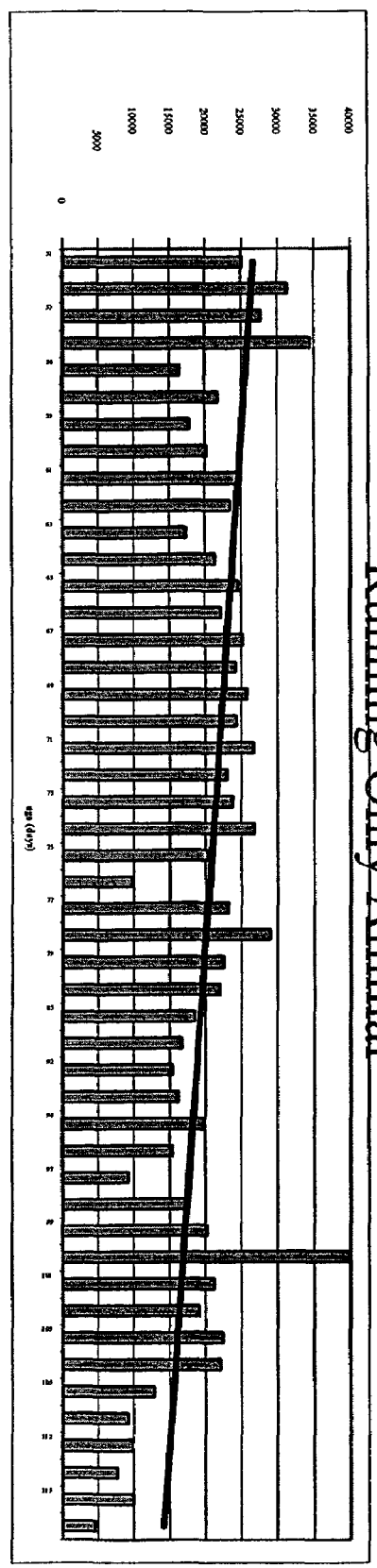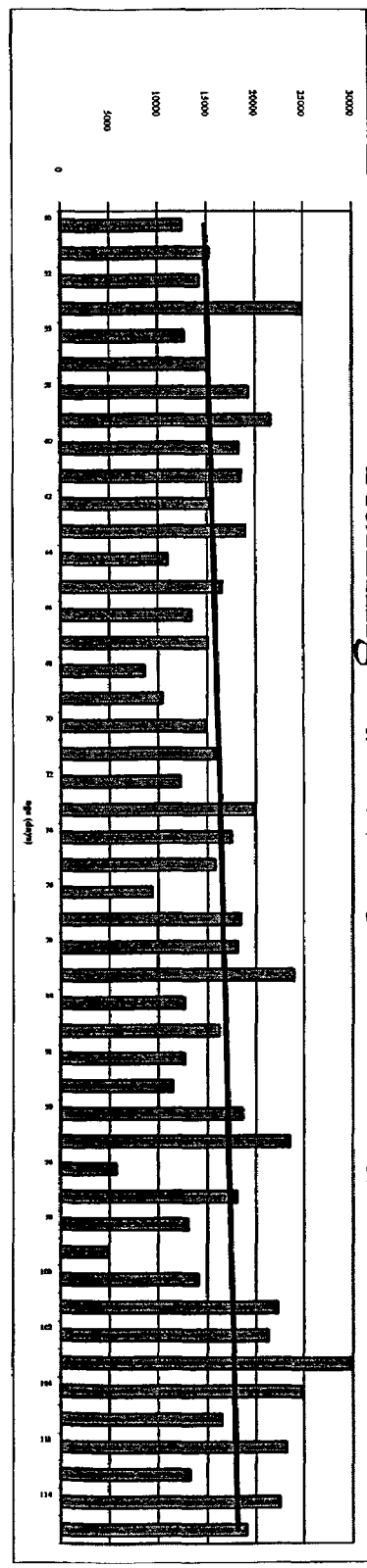
FIGURE 7B
FIGURE 7A

SEQUENCE LISTING

<160> NUMBER OF SEQ ID NOS: 2

<210> SEQ ID NO 1
<211> LENGTH: 20
<212> TYPE: DNA
<213> ORGANISM: Artificial Sequence -continued

```
<220> FEATURE:
<223> OTHER INFORMATION: 5' primer to an intron of human beta-globin

<400> SEQUENCE: 1
gtggatcctg agaacttcag                                              20

<210> SEQ ID NO 2
<211> LENGTH: 21
<212> TYPE: DNA
<213> ORGANISM: Artificial Sequence
<220> FEATURE:
<223> OTHER INFORMATION: 3' primer to an intron of human beta-globin

<400> SEQUENCE: 2
aagtcgtgct gcttcatgtg g                                            21
```

TARGETED RETROGRADE GENE DELIVERY TO MOTOR NEURONS

RELATED APPLICATIONS

This application is a continuation-in-part of U.S. application Ser. No. 10/032,047 entitled "RETROGRADE GENE DELIVERY" and filed on Dec. 21, 2001.

GOVERNMENTAL INTERESTS

This invention was developed with partial government support under grant number AG10435 from the National Institutes of Health. The government may have rights in this invention.

BACKGROUND OF THE INVENTION

1. Field of the Invention

The present invention relates to a method for delivering heterologous genes to motor neuron cell bodies using retrograde viral transport. In greater detail, the present invention relates to a method for introducing genes into neurons that innervate muscle tissues by using an adeno-associated virus vector that is capable of retrograde axonal transport. Following introduction, these genes can be expressed in the cell body of the neuron. This method has applications in the treatment of neurodegenerative diseases.

2. Background

A significant number of people worldwide suffer from neurodegenerative diseases. Many of these diseases cause the degeneration of motor neurons, which in turn results in the progressive loss of function of the muscle tissues which are innervated by these motor neurons. A number of neurodegenerative diseases which result in the loss of muscle function are known. Examples of such diseases include muscular dystrophy (MD) and amyotrphic lateral sclerosis (ALS). MD refers to a group of genetic diseases characterized by progressive weakness and degeneration of the skeletal or voluntary muscles which control movement. Although the severity of MD varies depending on type, it is often fatal due to respiratory deficit. ALS occurs when specific nerve cells in the brain and spinal cord that control voluntary movement gradually degenerate. The loss of these motor neurons causes the muscles under their control to weaken and waste away, leading to paralysis and eventually death due to paralysis of the muscles involved in respiration. In the United States, ALS affects at least 20,000 individuals.

As more becomes known about the genetic causes of neurodegenerative diseases, the utility of gene therapy as a treatment for such diseases increases. One component of any gene therapy program is delivery of the desired genetic material, such as a replacement gene, to the cells of interest. Neurons present feasible targets for gene delivery, however, given the structure and internal location of most neurons, administration of the gene delivery vector directly to a target neuron is often difficult. For example, intracranial injection must deliver the vector to a specific location without damaging the targeted cells or causing collateral infection of nearby cells. This precision of delivery is difficult to achieve since many target neuronal populations are physically intermixed with many different neurons. In addition, many target neuronal populations are effectively inaccessible using current delivery methods. Accordingly, there exists a need for a method which can be used to conveniently provide a gene delivery vector to a target neuron where access to target neuron is restricted. The invention described herein provides such a mechanism.

SUMMARY OF THE INVENTION

One embodiment of the invention is a method for delivering a heterologous gene to a cell body of a neuron. This method includes contacting a muscle tissue innervated by the neuron with a viral vector comprising a heterologous gene, wherein the viral vector enters the neuron and is retrogradely moved to the cell body.

Another embodiment of the invention is a method for treating a neurodegenerative disease in a subject in need thereof, wherein the disease affects a target neuron. This method includes: contacting a muscle tissue innervated by the target neuron with a viral vector comprising a heterologous gene, wherein the viral vector enters said neuron and is retrogradely moved to said cell body, and wherein expression of the heterologous gene results in a reduction in the neurodegenerative disease. In one aspect, the neurodegenerative disease is amyotrophic lateral sclerosis.

Yet another embodiment of the invention is a method for expressing a protein that is secreted from a target neuron, which includes contacting a muscle tissue innervated by the neuron with a viral vector comprising a heterologous gene encoding the protein, wherein the viral vector enters said neuron and is retrogradely moved to the cell body where the gene is expressed.

Still another embodiment of the invention is a method of treating a mammal having a neurodegenerative disease. In this embodiment, the mammal is treated by selecting a muscle that participates in respiration in the mammal, wherein said muscle is innervated by a target neuron comprising a synaptic region and a cellular portion; and contacting a muscle that participates in respiration in the mammal with a viral vector comprising a heterologous gene, wherein the viral vector enters a synaptic region of said neuron and is retrogradely moved to the cell body of the target neuron wherein expression of the gene modulates respiration.

A method for delivering a heterologous gene to a cell body of a neuron, comprising contacting a muscle tissue innervated by said neuron with a viral vector comprising a heterologous gene, wherein said viral vector enters a synaptic region of said neuron and is retrogradely moved to the cell body.

BRIEF DESCRIPTION OF THE DRAWINGS

FIGS. 7A–7B are graphs comparing the running ability of ALS mice treated with AAV-IGF-1 at 90 days of age (8A) compared to the running ability of nontreated ALS mice (8B).

DETAILED DESCRIPTION

Figure 1:
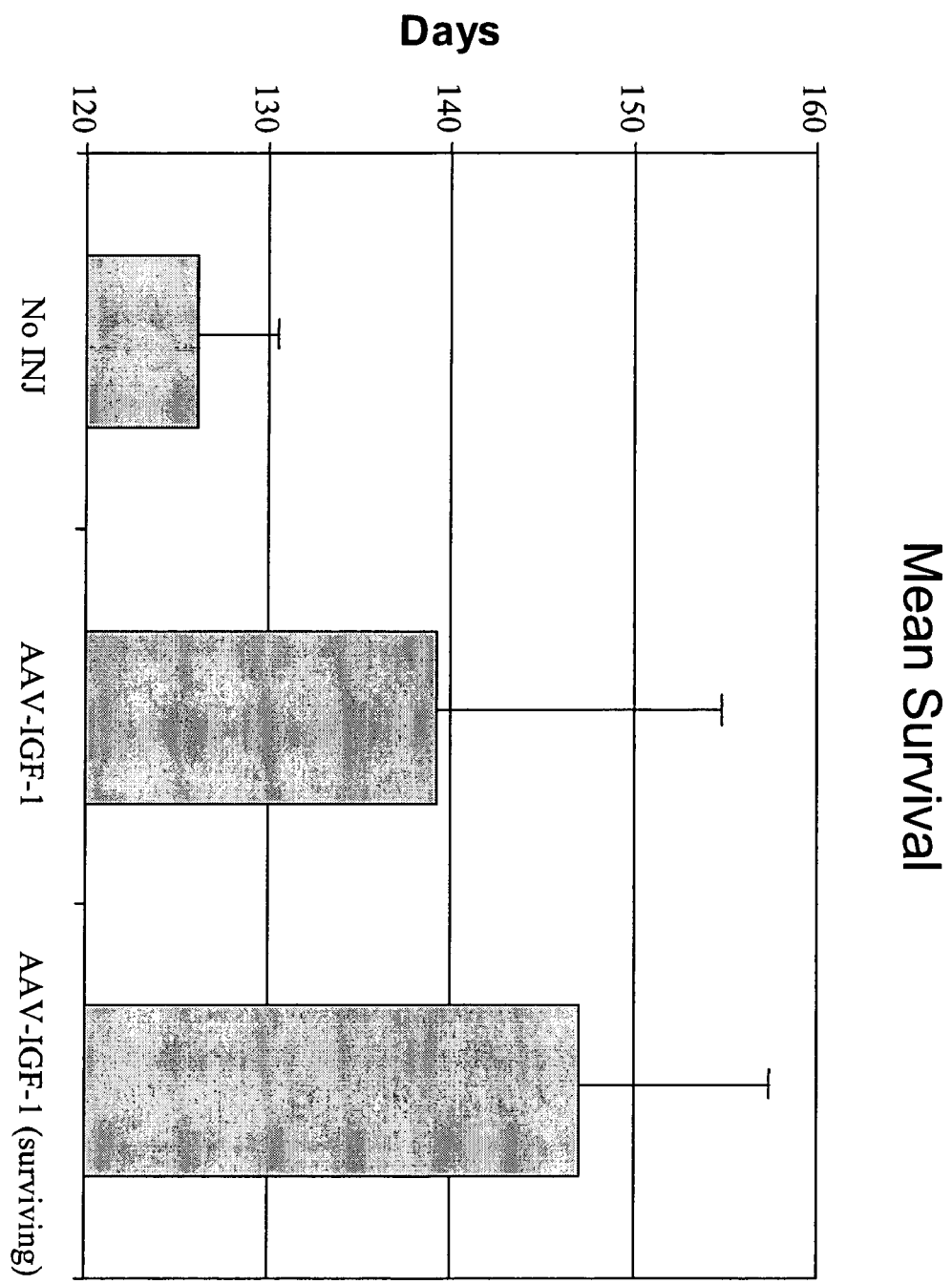
FIG. 1 is a graph comparing the mean survival times for ALS mice receiving intermuscular injections of AAV-IGF-1 with the survival times for mice receiving no treatment.

Embodiments of the invention described herein relate to methods for delivering heterologous genes to a cell body of a neuron by contacting muscle tissue innervated by the neuron with a vector having the heterologous gene. It was discovered that contacting muscle tissue with a heterologous gene resulted in retrograde transportation of the heterologous gene to the cell body of the neuron. In one embodiment, the heterologous gene is contained within a viral vector so that administering the viral vector via direct injection into the innervated muscle tissue results in stable transduction of the heterologous gene into the neuron cell body. Moreover, although some embodiments of the invention include expression of the heterologous gene once it reaches the cell body, the invention is not limited to expressing the heterologous gene. For example embodiments of the invention include retrogradely transporting the gene to the cell body without resultant expression. As discussed in detail below, preferred heterologous genes include genes encoding trophic factors and anti-apoptotic factors.

It should be realized that contacting the muscle includes any method for providing the heterologous gene to the muscle tissue. It is not required to provide to the heterologous gene directly into the muscle cell for it to be retrogradely transported to the cell body of the neuron. It was discovered that simply contacting the muscle bundle, or muscle tissue, with the heterologous gene was sufficient to induce retrograde delivery of the gene to the cell body. Accordingly, the invention should not be construed to require direct injection of the genetic material into a muscle cell.

The vectors which are introduced into the muscle tissues are taken up by the synaptic regions of these muscle-associated neurons and then transported along the axon of the neuron in a direction opposite the action potential (retrograde transport) and into the body (cellular portion) of the neuron. As used herein, "taken up" is meant to imply either a passive or an active mechanism for moving the vectors into the synaptic end of the neuron. Examples of such mechanisms are receptor mediated processes, endocytosis and vesicle mediated processes. Once present in the cell body of the neuron, the heterologous genes delivered by the vector are transported into the nucleus where they were found to be expressed by the neuron.

Other embodiments of the invention relate to methods for treating neurodegenerative diseases in a patient, wherein the disease affects a particular target neuron. In this embodiment muscle tissue innervated by the target neuron is contacted with a vector having a heterologous gene. The vector enters the neuron and is then retrogradely moved to the cell body of the target neuron. Once the heterologous gene has entered the cell body, it is transported to the nucleus and then expressed. The expression of particular heterologous genes was found to result in a reduction in said neurodegenerative disease. These experiments are described in detail below.

In one embodiment, the invention provides methods of treating Amyotrophic Lateral Sclerosis (ALS) by administering to a patient an viral vector carrying a therapeutically effective amount of a gene encoding insulin-like growth factor I (IGF-1). In this embodiment, the vector, termed herein "AAV-IGF-1" is preferably administered to a patient's diaphram muscles so that it is retrogradely transported to the cell bodies of the neurons that control the diaphram muscles. As is known, one of the leading causes of death among ALS patients is their inability to breath due to degeneration of the nerves and muscles that control breathing. This treatment can prevent, or reduce the instance, of such clinical indications by directly administering the trophic factor IGF-1 to the nerve cells controlling breathing.

In some embodiments of the present invention, the heterologous gene that is administered to a patient can be associated with signal sequences that directed the expressed protein to be secreted following expression. Expression of the secreted protein can be, for example, constitutive or regulatable. Thus, administration of a gene delivery vector into a muscle facilitates the secretion of a protein at a site that is distant from the site of injection. This is especially useful for delivering trophic factors to the tissue surrounding the cell body.

The term amino acid or amino acid residue, as used herein, refers to naturally occurring L amino acids or to D amino acids as described further below with respect to variants. The commonly used on- and three-letter abbreviations for amino acids are used herein (Bruce Alberts et al., *Molecular Biology of the Cell*, Garland Publishing, Inc., New York (3d ed. 1994)).

The term "disease state" refers to a physiological state of a cell or of a whole mammal in which an interruption, cessation, or disorder of cellular or body functions, systems, or organs has occurred.

The term "treat" or "treatment" refer to both therapeutic treatment and prophylactic or preventative measures, wherein the object is to prevent or slow down (lessen) an undesired physiological change or disorder, such as the development or spread of cancer. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

"Mammal" for purposes of treatment refers to any animal classified as a mammal, including humans, domestic and farm animals, and zoo, sports, or pet animals, such as dogs, horses, cats, cows, etc. Preferably, the mammal is human.

Retrograde Transport

Embodiments of the invention relate to methods for stably transfecting neuronal cells through retrograde transport of viral particles through the axon to the nucleus. By administering the proper dose of viral vectors carrying a gene of interest to a particular site, it was discovered that these vectors were capable of retrograde transport and stable transduction of the neuron. Herein, what is meant by "retrograde transport" is uptake of the vector at the axon terminal, and transport through the axon in a direction opposite to the direction of propagation of action potentials (and thus "retrograde") and into the body of the neuron in which the viral particles enter the nucleus, underwent single strand synthesis, and became transcriptionally and translationally active.

Such delivery is advantageous in many cases in which the projection neurons themselves are inaccessible, but their terminal projection fields, which define the neurons, are available for delivery of the genetic vector. Successful delivery to such a terminal projection field of a genetic vector capable of retrograde transport would thus result in retrograde transport and infection of the vulnerable projection neurons. In addition to delivering therapeutic transgenes, the identification of such viral transport mechanisms may advance study of CNS circuitry by combining neural tracing with functional modulation of targeted populations resulting from expression of experimental transgenes to effect a gain or loss of function.

Treatment of Neurodegenerative Diseases

Embodiments of the invention involve delivery of a substantially nontoxic, recombinant adeno-associated virus vector having a heterologous gene of interest in order to provide retrograde gene delivery with stable gene expression. Such a vector can be employed in retrograde gene mapping if a marker gene is packaged in the vector. Alternatively, such a vector can be used for the retrograde delivery of a therapeutic gene, such as a growth factor, an anti-apoptotic gene, or an antisense gene. Such therapeutic use would be especially advantageous where the target neuron population is distributed or difficult to reliably access, such as in the central nervous system. For example, therapeutic gene-bearing vectors can be delivered to the hippocampus or striatum, which results in the infection of projection neurons in the entorhinal cortex and the substantia nigra. This demonstrates a targeted delivery strategy of potential use for gene therapy of neurodegenerative diseases, such as Alzheimer's and Parkinson's diseases. Furthermore, an anti-apoptotic gene such as Bcl-xL can be delivered in vivo to a pathway-specific projection neuron population and the retrograde transport, infection, and expression of this gene product can protect these targeted neurons from subsequent injury. Neuroprotective (antiapoptotic) signaling pathways involving neurotrophic factors, cytokines and "conditioning responses" can counteract the effects of aging and genetic predisposition in neurodegenerative disorders. Thus, targeted delivery of anti-apoptotic genes to vulnerable projection neurons may be a useful neuroprotective strategy for early stages of neurodegenerative disease.

By greatly increasing the viral titer at the point of delivery, it was possible to effect retrograde stable transduction of neurons projecting to the delivery field of the AAV vector. This retrograde transport is thought to be mediated by the microtubules of the axon after uptake of the AAV vector at the axon terminal.

It should be noted here that the way in which viral titers are measured in the literature is not standardized. One method involves simply assessing the number of virions containing the viral genome, regardless of infectivity or functionality, using DNA dot blot, Southern blot, or semi-quantitative PCR. These numbers are generally reported as "particles/ml." An assessment of the viral titer using an infectious center assay, in which the rAAV is infected into cells with sufficient helper virus (wild-type AAV and adenovirus) to allow rAAV amplification, provides the number of infectious and replication-competent rAAV particles. This number is generally reported as "infectious units (or infectious particles)/ml." Lastly, an assessment of the viral titer using a rAAV transgene functional assay, which assesses specific transgene expression, provides the number of "transducing units/ml."

Previous experimental use of recombinant AAV vectors have involved relatively low viral titers and have assessed infection of local neurons or anterograde neuronal tracing only. In contrast, embodiments of the invention include methods of raising the virus titer at the point of delivery to preferably $1 \times 10^7$ infectious particles, or more preferably $1 \times 10^8$ infectious particles or more, and most preferably $1 \times 10^9$ infectious particles or more. By using these titer levels, it was possible to detect retrograde transduction of neurons projecting to the delivery field of the AAV vector. Thus, by using a marker gene we were able to identify the nucleus, cell body, and projections for each nerve cell that projected into a predetermined location.

Embodiments of the invention, however, are not necessarily limited to the use of AAV vectors. Any genetic vector may be used to practice the methods disclosed in this application. Of course, the vector should be substantially nontoxic to the contacted cells and enable stable, long-term gene expression. Such vectors may include, for example, lentivirus vectors, liposomal vectors, and the like (see, e.g., Latchman & Coffin, Rev Neurosci. (2001) 12(1):69–78, incorporated by reference herein).

In addition, it is possible to improve the qualities of the rAAV vector by methods well-known in the art, such as chemical modification of the AAV virion structure or capsid gene shuffling. Such methods may be employed to develop AAV strains with new tropism, such as tropism towards axon terminal receptors, as well as strains resistant to naturally occurring neutralizing antibody. Such methods are well within the capabilities of those of ordinary skill in virology.

In accordance with yet another embodiment of the present invention, there are provided methods of treating a neurological disease (including injuries, dysfunctions and disorders) in a mammal comprising administering a therapeutically effective amount or an effective amount of vectors as described herein. The present invention concerns the therapeutic application of vectors as described herein to enhance survival of neurons and other neuronal cells in both the central nervous system and the peripheral nervous system. The ability of vectors as described herein to regulate neuronal differentiation and survival during development of the nervous system and also in the adult state indicates that vectors as described herein can be reasonably expected to facilitate control of adult neurons with regard to maintenance, functional performance, and aging of normal cells; repair and regeneration processes in chemically or mechanically lesioned cells; and prevention of degeneration and premature death which result from loss of differentiation in certain pathological conditions.

In light of this understanding, embodiments of the present invention specifically contemplate applications of vectors containing heterologous genes to the treatment of (prevention and/or reduction of the severity of) neurological conditions deriving from injuries, diseases or disorders, including: (i) acute, subacute, or chronic injury to the nervous system, including traumatic injury, chemical injury, vasal injury and deficits (such as the ischemia resulting from stroke), together with infectious/inflammatory and tumor-induced injury; (ii) aging of the nervous system, including Alzheimer's disease; (iii) chronic neurodegenerative diseases of the nervous system, including Parkinson's disease, Huntington's chorea, amylotrophic lateral sclerosis, and the like, as well as spinocerebellar degenerations; (iv) chronic immunological diseases of the nervous system or affecting the nervous system, including multiple sclerosis; (v) disorders of sensory neurons as well as degenerative diseases of the retina; and the like.

CNS disorders encompass numerous afflictions such as neurodegenerative diseases (e.g. Alzheimer's and Parkinson's), acute brain injury (e.g. stroke, head injury, cerebral palsy) and a large number of CNS dysfunctions (e.g. depression, epilepsy, and schizophrenia). In recent years neurodegenerative disease has become an important concern due to the expanding elderly population which is at greatest risk for these disorders. These diseases, which include Alzheimer's Disease, Multiple Sclerosis (MS), Huntington's Disease, Amyotrophic Lateral Sclerosis, and Parkinson's Disease, have been linked to the degeneration of neural cells in particular locations of the CNS, leading to the inability of these cells or the brain region to carry out their intended function.

Further disease conditions contemplated for treatment in accordance with the invention include cerebral ischemia, chronic neurodegeneration, psychiatric disorders, schizophrenia, mood disorders, emotion disorders, disorders of extrapyramidal motor function, obesity, disorders of respiration, motor control and function, attention deficit disorders, concentration disorders, pain disorders, neurodegenerative disorders, epilepsy, convulsive disorders, eating disorders, sleep disorders, sexual disorders, circadian disorders, drug withdrawal, drug addiction, compulsive disorders, anxiety, panic disorders, depressive disorders, skin disorders, retinal ischemia, retinal degeneration, glaucoma, disorders associated with organ transplantation, asthma, ischemia, astrocytomas, and the like. Further examples of disorders include Alzheimer's disease, Amyotrophic Lateral Sclerosis (ALS) and Parkinson's disease.

Many neurological disorders are associated with degeneration of discrete populations of neuronal elements and may be treatable with a therapeutic regimen which includes vectors as described herein. For example, Alzheimer's disease is associated with deficits in several neurotransmitter systems, both those that project to the neocortex and those that reside with the cortex. For instance, the nucleus basalis in patients with Alzheimer's disease were observed to have a profound (75%) loss of neurons compared to age-matched controls. Although Alzheimer's disease is by far the most common form of dementia, several other disorders can produce dementia. Several of these are degenerative diseases characterized by the death of neurons in various parts of the central nervous system, especially the cerebral cortex. However, some forms of dementia are associated with degeneration of the thalamus or the white matter underlying the cerebral cortex. Here, the cognitive dysfunction results from the isolation of cortical areas by the degeneration of efferents and afferents. For example, Huntington's disease involves the degeneration of intrastriatal and cortical cholinergic neurons and GABAergic neurons (see, e.g., Hefti et al., Ciba Found Symp. (1996)196:54–69; Koliatsos V. E., Crit Rev Neurobiol (1996) 10(2):205–38). Pick's disease is a severe neuronal degeneration in the neocortex of the frontal and anterior temporal lobes, sometimes accompanied by death of neurons in the striatum. Treatment of patients suffering from such degenerative conditions can include the application of vectors as described herein, in order to manipulate, for example, the de-differentiation and apoptosis of neurons which give rise to loss of neurons. In preferred embodiments, the vectors as described herein are stereotactically provided within or proximate the area of degeneration.

In addition to degenerative-induced dementias, a preparation of invention vectors can be applied opportunely in the treatment of neurodegenerative disorders which have manifestations of tremors and involuntary movements. Parkinson's disease, for example, primarily affects subcortical structures and is characterized by degeneration of the nigrostriatal pathway, raphe nuclei, locus cereleus, and the motor nucleus of vagus. Ballism is typically associated with damage to the subthalmic nucleus, often due to acute vascular accident. Also included are neurogenic and myopathic diseases which ultimately affect the somatic division of the peripheral nervous system and are manifest as neuromuscular disorders. Examples include chronic atrophies such as amyotrophic lateral sclerosis, Guillain-Barre syndrome and chronic peripheral neuropathy, as well as other diseases which can be manifest as progressive bulbar palsies or spinal muscular atrophies. The present method is amenable to the treatment of disorders of the cerebellum which result in hypotonia or ataxia, such as those lesions in the cerebellum which produce disorders in the limbs ipsilateral to the lesion. For instance, a preparation of invention vectors can be used to treat a restricted form of cerebellar cortical degeneration involving the anterior lobes (vermis and leg areas) such as is common in alcoholic patients.

Other forms of neurological impairment can occur as a result of neural degeneration, such as amyotrophic lateral sclerosis and cerebral palsy, or as a result of CNS trauma, such as stroke and epilepsy. ALS is a name given to a complex of disorders that comprise upper and lower motor neurons. Patients may present with progressive spinal muscular atrophy, progressive bulbar palsy, primary lateral sclerosis, or a combination of these conditions. The major pathological abnormality is characterized by a selective and progressive degeneration of the lower motor neurons in the spinal cord and the upper motor neurons in the cerebral cortex. The therapeutic application of invention vectors prevents and/or reverses motor neuron degeneration in ALS patients.

Other Treatments

In addition to neurodegenerative diseases, acute brain injuries often result in the loss of neural cells, the inappropriate functioning of the affected brain region, and subsequent behavior abnormalities. Probably the largest area of CNS dysfunction (with respect to the number of affected people) is not characterized by a loss of neural cells but rather by abnormal functioning of existing neural cells. This may be due to inappropriate firing of neurons, or the abnormal synthesis, release, and processing of neurotransmitters. These dysfunctions may be the result of well studied and characterized disorders such as depression and epilepsy, or less understood disorders such as neurosis and psychosis.

The vectors of the present invention can also be used in the treatment of autonomic disorders of the peripheral nervous system, which include disorders affecting the innervation of smooth muscle and endocrine tissue (such as glandular tissue). For instance, invention vectors may be useful to treat tachycardia or atrial cardiac arrythmias which may arise from a degenerative condition of the nerves innervating the striated muscle of the heart.

In addition, invention vectors may be employed to support, or alternatively, antagonize the survival and reprojection of several types of central and peripheral ganglionic neurons, sympathetic and sensory neurons, as well as motor neurons (See, e.g., Terenghi G., J Anat (1999) 194 (Pt 1):1–14). To illustrate, such therapeutic vectors may be useful in treatments designed to rescue, for example, retinal ganglia, inner ear and accoustical nerves, and motorneurons, from lesion-induced death as well as guiding reprojection of these neurons after such damage. Such diseases and conditions include CNS trauma, infarction, infection (such as viral infection with varicella-zoster), metabolic disease, nutritional deficiency, toxic agents (such as cisplatin treatment), and the like. Moreover, certain of the vectors described herein (probably antagonistic forms) may be useful in the selective ablation of sensory neurons, for example, in the treatment of chronic pain syndromes.

Accordingly, there are provided methods of treating neuronal trauma in a mammal comprising administering a therapeutically effective amount of invention vectors as described herein. As used herein, the term "Neuronal trauma" refers to any injury to neuronal tissue produced by an exogenous event such as, for example, blunt force or other sudden physical impact that results in neuronal injury or death, either directly or through the abnormal release by dying neurons of toxic levels of endogenous neurotransmitters or metabolites thereof, e.g., glutamate. Neuronal trauma also refers to decreased neurotransmitter production, or a compromise in neuronal function (See, e.g., Fawcett J. W., Spinal Cord (1998) 36(12):811–7).

The vectors of the present invention can also be used in nerve prostheses for the repair of central and peripheral nerve damage. In particular, where a crushed or severed axon is entubulated by use of a prosthetic device, invention vectors can be added to the prosthetic device to increase the rate of growth and regeneration of the dendritic processes. Exemplary nerve guidance channels are described in U.S. Pat. Nos. 5,092,871 and 4,955,892. Accordingly, a severed axonal process can be directed toward the nerve ending from which it was severed by a prosthesis nerve guide which contains invention vectors.

In yet another embodiment, invention vectors can be used in the treatment of neoplastic or hyperplastic transformations, particularly of the central nervous system and lymphatic system. For instance, certain trophic factors are known to have mitotic or apoptotic activity. Thus, certain invention vectors are capable of inducing differentiation of transformed neuronal cells to become post-mitotic or possibly apoptotic. Treatment with certain invention vectors may involve disruption of autocrine loops, such as TGF-beta or PDGF autostimulatory loops, believed to be involved in the neoplastic transformation of several neuronal tumors. Invention vectors may, therefore, be of use in the treatment of, for example, malignant gliomas, medulloblastomas, neuroectodermal tumors, and ependymonas.

Yet another aspect of the present invention concerns the application of the discovery that invention vectors are likely induction signals involved in other vertebrate organogenic pathways in addition to neuronal differentiation as described above, having potential roles in other ectodermal patterning, as well as both mesodermal and endodermal differentiation processes. Thus, it is contemplated that invention vectors can also be utilized for both cell culture and therapeutic methods involving generation and maintenance of non-neuronal tissue, such as in controlling the development and maintenance of tissue from the digestive tract, liver, lungs, and other organs which derive from the primitive gut, as well as dorsal mesoderm-derived structures including muscular-skeletal tissues and connective tissue of the skin; intermediate mesoderm-derived structures, such as the kidney and other renal and urogenital tissues; and head mesenchymal and neural crest-derived tissue, such as cephalic connective tissue and skull and branchial cartilage, occular tissue, muscle and cardiac tissue (see, e.g., Carver and Barness, Clin Perinatol (1996) 23(2):265–85). This should not be construed as a comprehensive list, and other tissues and diseases that may be affected by the invention vectors are envisaged. For example, memory loss or memory enhancement is encompassed as a potential target for invention vectors (see, e.g., Calamandrei and Alleva Behav Brain Res Jan. 23, 1995;66(1–2):129–32). Those of skill in the art will readily recognize additional applications of invention vectors based on the components of the invention vectors, e.g., the activities and, thus, the applications of trophic factors (which have been well characterized and are known to those of skill in the art (Yuen et al., Ann Neurol. (1996) 40(3): 346–54)).

Treatment of Muscle-Related Neurodegenerative Diseases

Many neurodegenerative diseases are associated with a progressive loss of muscle function. This loss of muscle function results from the degeneration of neurons which innervate the affected muscle tissue. In some cases, muscle function can be restored and in many cases further loss of function can be prevented by introduction and expression of an appropriate gene within neurons that innervate the affected muscle tissue.

Neurons have shown much potential as gene delivery targets, however, introduction of genes into these cells is often challenging because of their cellular architecture and their location with the body. In many cases, the "cell body" or "cellular portion" (portion containing the nucleus) of the neuron is totally inaccessible to contact with the gene or gene delivery vector. Synaptic regions of motor neurons are associated with muscle tissues which they innervate. Muscle tissues are generally accessible for the administration of agents, such as gene delivery vectors, via intermuscular injection. Accordingly, intermuscular injection provides a route by which the synaptic regions of target neurons can be contacted which a gene delivery vector. As used herein, intermuscular injection includes injection between groups of muscle fibers and also includes injection adjacent a muscle group.

Selection of muscle tissue that is innervated by neurons that are affected by a neurodegenerative disease is an intial step in the treatment of the disease. Relationships between specific motor neurons and the muscle tissues which they innervate are known. For example, there are several known classes of motor neurons, such as the Spinal Cord motor neurons, cranial motor neurons and the brain stem motor neurons. Each of these classes of motor neurons are known to innervate particular muscle groups. Thus, in order to treat a particular set of motor neurons that are degenerating, a physician would only need to determine which muscles are innervated by the neurons and then contact those muscles with a vector that will retrogradely move to the cell body. In one embodiment, the vector includes an anti-apoptotic gene that prevents the cell from dying. In another embodiment, the vector includes a heterologous gene that encodes a wildtype version of a protein in order to replace a defective allele of the same gene in the cell body. In still another embodiment, the heterologous gene is a neurotrophic factor that promotes cell growth.

Examples of trophic factors include, but are not limited to, Agrin, Amphiregulin, Aria, Artemin, BDNF, Cardiotrophin-1, Ciliary neurotrophic factor, c-kit, c-ret, CSF-1, EGF, FGFs: 1, 2, 5, FLT3L, GDNF G-CSF, GM-CSF, Hedgehog, Heregulin (Neuregulin), IGF 1, 2, Interleukin: 2, 3, 4, 5, 6, 7, 9, 11, 12, 13, 15, Leptin, LIF, Midkine, MuSK, Myostatin (GDF 8) NGF, Netrins, Neurturin, NT3, NT4/5, p75, Pleiotrophin, PDGF, Persephin, Saposin C, Stem cell factor, trk A; B; C, and TGF α and β.

Treatment of ALS in Mammals

Amyotrophic lateral sclerosis (ALS) is a prevalent, adult-onset neurodegenerative disease affecting nearly 5 of 100,000 individuals. The disease, first characterized by Charcot in 1869, is a neurodegenerative process selective to motor neurons connecting the brain to the spinal cord and spinal cord to muscles. The neurons typically affected are located in the lower motor neurons of the brainstem and spinal cord and upper motor neurons in the cerebral cortex.

Within 2 to 5 years after clinical onset, the loss of motor neurons leads to progressive atrophy of skeletal muscles, which results in loss of muscular function resulting in paralysis, speech deficits, and death due to respiratory failure. The genetic defects that cause or predispose ALS onset are unknown, although missense mutations in the SOD-1 gene occurs in approximately 10% of familial ALS cases, of which up to 20% have mutations in the gene encoding Cu/Zn superoxide dismutase (SOD1), located on chromosome 21. SOD-1 normally functions in the regulation of oxidative stress by conversion of free radical superoxide anions to hydrogen peroxide and molecular oxygen. To date, over 90 mutations have been identified spanning all exons of the SOD-1 gene. Some of these mutations have been used to generate lines of transgenic mice expressing mutant human SOD-1 to model the progressive motor neuron disease and pathogenesis of ALS.

One high expressing mutant SOD-1 mouse (13-fold above endogenous SOD-1) contains an amino acid substitiution of glycine at position 93 by alanine (G93A) in the SOD-1 protein. This mouse model is paralyzed in multiple limbs due to motor neuron cell death in the spinal cord and contains membrane-bound vacuoles in cell bodies and dendrites, which most likely result from degenerating mitochondria (Gurney, et al. (1994) *Science* 264:1772–5). Leg muscles from end-stage rats have atrophic myofibers and display obvious hindlimb paralysis or paresis in which compound motor action potentials by EMG recordings show markedly reduced amplitudes as well as continuous fibrillation potentials and positive sharp waves compared to wildtype animals. Hematoxylin and Eosin stained sections of end-stage animals reveals dense gliosis with a complete loss of ventral large motor neurons as well as atrophied ventral roots. Degeneration of most axons consists of macrophage infiltration and aggregates of SOD-1 co-localized with ubiquitin as well as accumulation of neurofilaments. Onset of disease progression typically appears as hindlimb abnormal gait which progresses quickly (1–2 days) to overt hindlimb paralysis, typically affecting one limb first. Within 1–2 days, the second hindlimb is involved although the animals can use their forepaws normally. Affected animals show signs of weight loss, poor grooming, and porphyrin staining around the eyes in which the animals progress to end-stage of the disease within 11 days after onset of symptoms. These animals die by 4 to 5 months of age.

However, as described in the following examples, it was discovered that treatment of muscle tissuse in the SOD-1 mouse with AAV carrying a gene encoding Insulin-like growth factor I (Igf-1) was found to slow progression of ALS in the mouse model. Specifically, injection of the AAV-IGF-1 into intercostal muscles of the mice was found to extend the life expectancy of the mice by over 20 days. In addition, AAV-IGF-1 was found to increase the grip strength of the mice and also to increase their ability to run for extended periods of time. More details on these experiments are provided below.

EXAMPLES

1. Production of Viral Vectors

In one experiment, an AAV vector carrying a green fluorescent protein (GFP) reporter gene, or a GFP gene fused to a gene encoding the Bcl-xL anti-apoptotic factor, was produced in the following manner. Recombinant AAV-2 carrying eGFP (available from Clontech, Cambridge, UK) or a GFP-Bcl-xL fusion (human Bcl-xL CDNA, obtained from J. Reed, Burnham Inst.) driven from the human CMV promoter was produced in HEK293 cells by calcium phosphate transient transduction of vector plasmid and pAAV/Ad8 helper plasmid, followed by infection with adenovirus dl312 (MOI 2.0). Virus was purified by two CsCl density gradients, dialysis, and heating to 56° C. for 1 hour. Recombinant virus titers were approximately $5 \times 10^{10}$ infectious particles per milliliter. All viral stocks were tested and found to be free from contaminating adenovirus. More information on these methods can be found in Senut et. al., *J Neurosci.* Jan. 1, 2000; 0(1):219–229. In addition, examples of methods for performing viral titers can be found in Snyder, et al. *Hum Gene Ther. Nov.* 1, 1997; 8(16):1891–900. A general review of biology, immunology and production of AAV can be found in, for example, Monahan & Samulski, Mol Med Today. (2000) 6(11):433–40, and Smith-Arica & Bartlett, Curr Cardiol Rep. (2001) 3(1):43–9 (each incorporated herein by reference).

2. Expression of Reporter Gene Following Viral Injection into Projection Fields

To test the hypothesis that therapeutic or experimental genes can be delivered to projection neurons by retrograde transport of viral particles, AAV containing GFP produced in the manner described above was injected into the hippocampus and striatum of rats. Specifically, F344 female rats (140–160 g; Harlan Sprague-Dawley) were deeply anesthetized and positioned in a stereotaxic frame for right-unilateral injection into the hippocampus (AP−4.0, ML−3.0, and DV−2.5 from dura) or striatum (AP+0.2, ML−3.0, and DV−4.0 from dura). Viral suspension (3 µl per site at $5 \times 10^{10}$ infectious particles/ml) was injected at a rate of 0.3–1.0 µl/min. Animals received either rAAV-GFP (hippocampus, n=12; striatum, n=6) or rAAV-Bcl-xL/GFP (hippocampus, n=12). Animals were transcardially perfused four weeks after viral injection with 4% paraformaldehyde and serial 50 µm thick horizontal sections (hippocampal-injected animals) or coronal sections (striatal-injected animals) by produced by freezing sliding microtomy.

Multiple immunofluorescent labeling used antibodies against NeuN (mouse, 1:50, R. Mullen, Univ. Utah), tyrosine hydroxylase (TH, rabbit, 1:1000, Chemicon), anti-GFAP (guinea pig, 1:1000, Advanced Immunochemical), anti-CD4 and CD8 (both mouse, 1:1000, Pharmingen), and anti-GFP (rabbit, 1:500, Clontech) to enhance detection of the reporter gene. Donkey anti-species antibodies conjugated to biotin, FITC, Cy3, or Cy5 and Streptavidin-FITC (1:250; all from Jackson Immunoresearch) were used for detecting primary antibodies. Fluorescent DNA stains used were DAPI (30 ng/ml), propidium iodide (PI, 1:1000), or ToPro3 (1:5000, all from Molecular Probes). Microscopy was performed using confocal microscopes (BioRad MRC1024UV or Olympus FluoView 200).

Within two weeks following this intrahippocampal injection of rAAV-GFP, there was robust expression of gene product in neurons of all hippocampal subfields with the greatest concentration of GFP-positive neurons in the dentate hilus. We discovered that there was anterograde GFP filling of hippocampal neurons, demonstrating neurotropic infection by AAV. Unilateral injection of AAV-GFP into the right hippocampus was found to infect neurons, as detected by antibodies against the neuronal marker NeuN (red), in all hippocampal subfields.

The GFP gene product (green) was found to fill neuronal cell bodies and anterogradely fill axonal processes, including commissural projections. The location of the perforant pathway lesion was also indicated. Infection was found in Area CA1 neurons, dentate granule neurons, and Area CA3 neurons. In addition, we discovered anterograde filling of hippocampal commissural projections to the non-injected hemisphere. Moreover, there was little infection of dentate granule neurons.

Infection of neurons was also demonstrated by the anterograde filling of processes with diffused GFP. Hilar mossy cells of the hippocampus project to the molecular layer of both the ipsilateral and contralateral granule cell layer, and, accordingly, GFP filled both ipsilateral and contralateral projections. There was little or no host immune response against the virus or GFP transgene, based on the absence of GFAP hypertrophy or of CD4/CD8-positive cells, nor was vascular cuffing observed.

The hippocampal formation receives input from various cortical, subcortical, and commissural projections. Preliminary observations of labeled projection neurons from these regions led the present inventors to a systematic evaluation of retrograde infection and transport following AAV delivery. Cortical input to the hippocampus arises from primarily glutamatergic projection neurons in layer II of the entorhinal cortex traveling via the perforant pathway to form the entorhinodentate projection. Within two weeks of rAAV-GFP delivery to the hippocampus, GFP was expressed in entorhinal layer II neurons. Intrahippocampal injection of AAV-GFP specifically infected entorhinal cortex projection neurons to the dentate gyrus in layer II (ECL2). Expression levels varied between individual layer II neurons; however, three-dimensional sampling using confocal microscopy revealed that more than 80% of layer II neurons expressed some GFP. The distribution and variable intensity of GFP-expression was similar to that which has been reported following intrahippocampal injection of a retrograde tracing dye.

Retrograde infection of projection neurons was less robust among other populations projecting to the AAV-injected hippocampus. Despite commissural projection of dentate hilar neurons to the contralateral dentate molecular layer, few hilar neurons in the contralateral hippocampus expressed GFP. We found that the dentate gyrus contralateral to the site of intrahippocampal AAV-GFP injection showed all cells labeled by propidium iodide (PI, red) and commissural projections filled with GFP (green). There were also few GFP-positive neurons from the subcortical projections to the hippocampus arising from the medial septum, which demostrated retrograde infection of medial septum projection neurons following intrahippocampal AAV-GFP injection.

To determine if retrograde infection was unique to hippocampal projections, AAV-GFP was injected into the striatum followed by examination of projection neurons within the substantia nigra pars compacta for expression of GFP. As described above, the dopaminergic nigrostriatal projection provides important modulatory input to the striatum and the progressive degeneration of this pathway produces the clinical manifestations of Parkinson's disease. As observed in the hippocampus, delivery of AAV in the striatum produced substantial infection of local neurons. Within two weeks of injection to the striatum, there was robust expression of GFP in tyrosine hydroxylase-positive neurons of the substantia nigra pars compacta,. No GFP expression was detected in the cerebral cortex of striatal AAV-injected animals, suggesting that retrograde infection from this delivery site may be specific to the nigrostriatal projection.

3. Confirmation of Infection by Viral Particles with Fluorescent Marker

To discriminate between retrograde transport of GFP protein and true infection of projecting neurons by retrogradely transported AAV viral particles, AAV particles conjugated to the fluorescent dye, Cy3, were injected into either the hippocampus or striatum. This was accomplished in the following manner.

For viral transport studies, rAAV-GFP was produced with pXX6, a helper plasmid for use in adenovirus-free AAV packaging, purified by four CsCl gradients to ensure high purity, and labeled with N-hydroxysuccinimidyl ester Cy3 reagent (Amersham). Animals received intracranial injection of Cy3-conjugated AAV (hippocampus, n=3; striatum, n=3) and were perfused 24 hours later. To discriminate between retrograde transport of GFP protein and true infection of projecting neurons by retrogradely transported AAV viral particles, AAV particles conjugated to the fluorescent dye, Cy3, were injected into either the hippocampus or striatum. Previous work has shown that careful conjugation of this probe does not alter the infectivity of the virus.

To demonstrate that labeled virus was fully infectious, HEK 293 cells were infected with Cy3-AAV-GFP. Confocal microscopic analysis showed that virus attached to the cell membrane within minutes; by 30 minutes, virus had localized within the nucleus, and GFP expression could be observed by 24 hours.

Examination of entorhinodentate and nigrostriatal projection neurons 24 hours following in vivo delivery of Cy3-conjugated AAV to the hippocampus and striatum, respectively, revealed the presence of Cy3 particles within the cytoplasm and nucleus of these projection neurons. Systematic sampling of the labeled region revealed that 65% of substantia nigra pars compacta neurons and 90% of entorhinal layer II neurons contained Cy3-conjugated viral particles. Intraventricular delivery of the microtubule depolymerizing agent, colchicine, completely blocked the retrograde transport of Cy3-conjugated AAV particles at 24 hours after injection, demonstrating that viral particles were moved by specific retrograde axonal transport. Furthermore, adjacent, non-projecting glial cells did not contain Cy3-conjugated AAV particles, suggesting that retrograde transport of viral particles had occurred by such an intracellular mechanism.

Examination of entorhinodentate and nigrostriatal projection neurons 24 hours following in vivo delivery of Cy3-conjugated AAV to the hippocampus and striatum, respectively, revealed the presence of Cy3 particles within the cytoplasm and nucleus of these projection neurons. We also discovered that AAV viral particles conjugated to the fluorophore Cy3 (red) in a population of entorhinal layer II cells were detected by the DNA stain ToPro3 (blue) following injection to the ipsilateral dentate gyrus. By merging images in of the Cy3 conjugated AAV viral particles with images of the neuronal marker, NeuN, we showed that the viral particles were located within entorhinal neurons. Also, AAV-Cy3 tagged virus injected into the striatum were detected in cells of the ipsilateral substantia nigra. By detecting with tyrosine hydroxylase (TH, green) we revealed the presence of viral particles within TH-positive nigral neurons.

There was sparse labeling of projection neurons in those regions (medial septum, contralateral hippocampus) with limited GFP expression. Systematic sampling found that 65% of substantia nigra pars compacta neurons and 90% of entorhinal layer II neurons contained Cy3-conjugated viral particles. Adjacent, non-projecting glial cells did not contain Cy3-conjugated AAV particles, suggesting that retrograde transport of viral particles had occurred by specific intracellular means. Intraventricular delivery of the microtubule depolymerizing agent, colchicine, completely blocked the retrograde transport of Cy3-conjugated AAV particles at 24 hours after injection demonstrating that viral particles were moved by specific retrograde axonal transport.

4. Confirmation of Active Transcription of Reporter Gene in Projection Neurons

To determine if GFP was actively transcribed in the projection neurons, RT-PCR analysis was performed two weeks following AAV delivery to the hippocampus or striatum. This was accomplished in the following manner. Tissue from hippocampal (n=2) or striatal (n=2) rAAV-GFP injected animals was collected after two weeks using RNase free materials and reagents. RNA was isolated from both the injection sites and projection neuron populations, in addition to a control region (cerebellum). Total RNA was isolated from the tissue using the RNAzol B reagent (Tel-Test, Inc.). Reverse transcription was performed with the Superscript kit (Life Technologies) using oligo dT primer. For amplification, the 5' primer; GTGGATCCTGAGAACTTCAG (SEQ ID NO:1) was homologous to the 5' untranslated region of the rAAV-GFP transcript, while the 3' primer; AAGTCGTGCTGCTTCATGTGG (SEQ ID NO:2) was homologous to GFP. These primers flank a human β-globin intron that is removed from the mRNA by splicing. Thirty cycles of PCR were performed (1 min. each at 94° C., 60° C., and 72° C.) using Taq DNA polymerase (Promega). PCR products were analyzed by electrophoresis on a 3% agarose gel. Amplification primers flanking an intervening sequence intron at the 5' end of the transcript were used to distinguish single stranded viral DNA from mRNA.

Amplification from single or double stranded viral genomic DNA generated a 900 base pair (bp) product in a control reaction using pAAV-GFP vector plasmid as the template, while mRNA processed to excise the intron yielded a 300 bp product. This RT-PCR analysis of viral expression revealed appropriate 300 bp transcripts in the substantia nigra of animals receiving striatal injections and in the entorhinal cortex of animals receiving hippocampal injections of AAV-GFP. At the site of injection, viral genomic DNA generated a 900 bp product in a control reaction using a pAAV-GFP vector plasmid.

Viral message was detected at high levels at the hippocampal and striatal injection sites of both animals, as well as at lower levels in the entorhinal cortex and substantia nigra. Viral genomic DNA was detected in both injection areas and faintly in one substantia nigra region. The viral transport studies and the RT-PCR data indicate that the virus was retrogradely transported from the injection sites, the recombinant viral genome was converted to double stranded DNA, mRNA was transcribed and spliced, and GFP was translated.

5. Expression of a Reporter Gene in Spinal Cord Neurons

Expression of the reporter gene is not limited to cranial neurons; the AAV vector is also capable of retrograde transport from an innervated muscle injection site into spinal motorneurons. Specifically, eAAV-EFGP (Enhanced Green Fluorescent Protein) was injected into the tibialis muscle of an adult mouse. Two weeks post injection, the muscle and spinal cord were evaluated for GFP expression. High level expression was found in the muscle and significant expression was found in the cell bodies of the spinal cord projected to the muscle. This indicates retrograde axonal transport of the virus within spinal motorneurons and demonstrates that the rAAV vector may be broadly employed in the retrograde infection of neurons throughout the CNS.

6. Use of rAAV-Mediated Retrograde Axonal Transport in Central Nervous System Mapping Infection, retrograde axonal transport, and stable expression of a reporter gene using a rAAV vector may be employed in order to conduct retrograde mapping of the central nervous system. In retrograde mapping, recombinant AAV vector bearing a reporter gene, such as the GFP gene employed in the examples above, may be delivered at the titers described above. Subsequent to delivery, the neurons projecting to the delivery field may be determined by the expression pattern of the reporter gene in the cell body. In the examples above, GFP was employed, but such mapping is not limited to the use of this gene; other fluorescent markers may be employed, or alternatively, the presence of the marker may be assessed by staining or using immunological techniques.

The use of a rAAV vector in such mapping offers significant advantages over previous vectors capable of retrograde transport. As noted above, such vectors, such as recombinant herpes simplex virus and recombinant pseudorabies virus, are often toxic to the cells infected and may provoke an immune response. Such inflammatory responses are damaging to CNS tissue and may lead to errors in mapping. Furthermore, the integrative and stable nature of the AAV virus allows mapping to be conducted for a relatively long period of time after delivery of the viral vector; expression of the transgene has been reported for a period of months to years after transduction.

As noted above, the methods disclosed herein are not limited to the use of AAV vectors. Thus, other vectors that are substantially non-toxic, capable of retrograde transport, and enable stable, long-term gene expression may also be employed. Potential vectors of this type are lentivirus vectors and liposomal vectors.

7. Viral Delivery of Therapeutic Genes Via Retrograde Transport a. Alzheimer's Disease: Intrahippocampal Delivery of an Anti-Apoptotic Factor It is possible to deliver a therapeutic gene to a specific population of projection neurons using the methods described above. For example, as noted above, entorhinal layer II neurons suffer severe degeneration early in the progression of Alzheimer's disease. By transecting the perforant pathway in a rodent model, it is possible to produce selective degeneration of layer II entorhinal neurons, thus providing an animal model for the progression of Alzheimer's.

AAV containing the anti-apoptotic gene (Bcl-xL) and a GFP reporter (AAV-Bcl-xL) was injected into a rat hippocampus to determine if expression of Bcl-xL would protect entorhinal layer II neurons from subsequent injury. Injection was carried out as described above, and evaluation of the protective effects of the viral injection was assessed as follows. Two weeks following viral injection, half of the hippocampal-injected animals (AAV-GFP, n=6; AAV-Bcl-xL/GFP, n=6) received right-unilateral perforant path lesions. Quantification of entorhinal layer II neuron number was performed on a one in six series of propidium iodide stained sections for each animal using the optical fractionator procedure (MicroBrightField, Inc., Lokhester, Vt.). Statistical analysis was performed by multi-way ANOVA followed by a Bonferroni post-hoc analysis of means differences between groups (GraphPad Software, San Diego, Calif.).

Virally delivered Bcl-xL was produced as a fusion protein with GFP to permit detection and localization of infected cells, since it is not possible to discriminate by immunocytochemical detection between endogenous rodent Bcl-xL and the transfected Bcl-xL gene product. To demonstrate that the Bcl-xL/GFP fusion protein was functional, HEK293 cells were infected with either AAV-GFP or AAV-Bcl-xL/GFP. The HEK293 cells were then treated with staurosporine or tyrphostin, which are known to cause apoptosis. It was determined that only the Bcl-xL/GFP gene product successfully protected cells from staurosporine- or tyrphostin-induced apoptotic cell death.

Within two weeks following injection of AAV-Bcl-xl/GFP into the hippocampus, entorhinal layer II neurons showed expression of GFP in a distribution and Intensity equivalent to that of animals treated with AAV-GFP. We found that entorhinal layer II projection neurons to the dentate gyrus formed a distinct band of cells in the uninjured entorhinal cortex. Projection neurons are large cells with an RNA-rich cytoplasm. Entorhinal neurons infected with the Bcl-xL/GFP construct were indistinguishable from cells infected by AAV-GFP alone in unlesioned animals. Layer II neurons appeared healthy after infection with either construct and quantitation revealed no cell loss following expression of the functional transgene, Bcl-xL in unlesioned animals.

Transduction of the perforant pathway produced significant death of entorhinal layer II neurons after two weeks in animals expressing only GFP, with over 60% loss of layer II neurons. However, quantitation of entorhinal layer II neurons showed no toxic effect of the Bcl-xL construct in unlesioned animals. Creating a perforant pathway lesion produced a significant 60% loss of GFP-expressing entorhinal neurons ($p<0.001$). In contrast, there were more than twice as many surviving neurons in animals that were first transfected with the AAV-Bcl-xL/GFP construct demonstrating significant protection by the Bcl-xL transgene ($p<0.01$). Surviving neurons still expressed GFP, but were shrunken and surrounded by apoptotic bodies and an increased population of glial cells. We also found that prior retrograde in vivo AAV gene delivery of the reporter gene, GFP, failed to protect vulnerable layer II neurons from subsequent lesion of the perforant pathway resulting in neuronal loss and atrophy of remaining neurons. Glial cell numbers were increased in response to injury and apoptotic bodies were seen in the cells transfected with the AAV-GFP construct. GFP was still expressed within surviving neurons. In contrast, expression of Bcl-xL protected entorhinal layer II neurons from the significant injury-induced death seen in animals transfected with the AAV-GFP construct. Entorhinal neurons appeared healthy and continued to express the Bcl-xl/GFP transgene. Thus, we found that in vivo, retrograde delivery of AAV-Bcl-xL/GFP protected entorhinal neurons from apoptosis due to a perforant pathway lesion. Individual entorhinal neurons appeared healthy and continued to express Bcl-xL/GFP. Despite neuronal sparing, there was still an increase in glial cell number. These data illustrate that expression of the anti-apoptotic gene, Bcl-xL, in targeted projection neurons will contribute to their survival following exposure to substantial injury.

b. Parkinson's Disease: Intrastriatal Delivery of an Apoptotic Factor

In one experiment we demonstrated that the AAV-GFP/Bcl-xL clone delivered to the striatum could protect against a Parkinson's Disease model. Adult rats were injected into the striatum with AAV-GFP/Bcl-xL, or saline as a control, two weeks prior to injection of 6-hydroxydopamine (6-OHDA), a specific neurotoxin to dopaminergic neurons within the substantia nigra pars compacta. Four weeks after delivery of 6-OHDA, the retrograde tracer fluorogold was injected into the striatum and animals were sacrificed 4 days later.

Nigral neurons were evaluated by fluorogold and TH immunohistochemistry. Quantification of nigral neurons within the substantia nigra pars compacta showed that normal, non-injected animals had approximately 13,000 fluorogold positive cells while the animal lesioned with 6-OHDA (n=1) and injected with saline (control) had 1,260 fluorogold positive cells. In contrast, the two animals that received AAV-GFP/Bcl-xL injections had 10,890 and 11,243 fluorogold positive cells indicating that retrograde delivery of AAV-GFP/Bcl-xL from the striatum to the nigra was protecting nigral-TH positive cells from being lesioned with 6-OHDA.

Similarly, other therapeutic genes, such as the Bcl-2 family of anti-apoptotic genes, can be packaged into such rAAV vectors (or other vectors such as the lentiviruses and liposomes described above to the extent such vectors are capable of retrograde transport) and employed to deliver these therapeutic genes to a person in order to treat Parkinson's and other diseases. For example, the Bcl-2 gene can be cloned into an AAV and transfected at high titer into the striatum to allow for retrograde transport and long-term transduction. Expression of Bcl-2 is then found, along with protection of the transfected cells against apoptosis.

ALS in Mice and Humans

ALS is known to be caused in both mice and human by mutations in the superoxide dismutase gene SOD1. Transgenic mice that develop an ALS-like syndrome have been generated from at least three of these SOD1 mutations. Two of these mutations, a glycine to arginine mutation at position 85 (G85R) and a glycine to alanine mutation at position 93 (G93A), have been shown to cause ALS in both humans and mice.

8. Retrograde Transport of AAV to the Spinal Cord of Wildtype and ALS Mice and Rats After Intermuscular Injection To determine whether transport of virus from axons innervating into skeletal muscle is feasible, AAV having the gene for GFP or GFP/Bcl-xL (AAV-GFP and AAV-GFP/Bcl-xL, respectively) were injected into hindlimb anterial tibialis muscles, intercostal muscles, or diaphragm of rats and mice. In these experiments, transport of the viral vector in spinal cord neurons of wildtype rats and mice was compared to transport in spinal cord neurons of rats and mice having a G93A mutation in the gene encoding SOD1. Both wildtype and G93A rats and mice were injected at ages between 90–100 days. Two to three weeks post injection, the animals were sacrificed and the spinal cords were removed and evaluated for GFP expression by cryostrat sectioning and histochemistry followed by confocal microscopy. The tissue analyses indicated that efficient retrograde transport of the virus occurred within the spinal motor neurons. In particular, virus was observed infecting myocytes at the injection site as well as spinal motor neurons. Virus encoding GFP injected into the hindlimb effectively transduced ventral horn motor neurons of the lumbar spinal cord as shown by fluorescent microscopy for GFP. Injection of the virus to intercostal muscles and diaphragm transduced cells within the thoracic and cervical spinal cord. These results demonstrate that genes that express therapeutic proteins can be efficiently delivered by retrograde transport at various times during the disease state in ALS animals.

9. The Efficiency of Retrograde Transport of Virus Vector and Subsequent Gene Expression in the Motor Neurons of the Spinal Cord is Affected by Vector Dose Injection of $1 \times 10^9$ infectious particles of AAV-EGFP into the tibialis muscle of wildtype mice resulted in a significant number of spinal motor neurons expressing EGFP two weeks after injection. The following experiments demonstrate the effect of increasing viral dose on the efficiency of retrograde transport of AAV containing enhanced GFP (AVV-EGFP) as measured by the expression of EGFP.

A range of concentrations of AAV-EGFP can be prepared by centrifugation through a 100 kDa filter (Centricon-100K). Doses of AAV-EGFP ranging from $1.0 \times 10^7$ to $1.0 \times 10^{12}$ are prepared in 20 µl and injected into the tibialis muscles, intercostal muscles, or diaphragms of both wildtype and G93A mutant mice at 90 days of age. Animals are evaluated three weeks post-injection for relative expression of EGFP at the site of injection (muscle), as well as at the projecting neurons of the spinal cord to evaluate the extent of retrograde transport and transgene expression. Immunohistochemistry is performed to define the phenotype of the cells that are transduced. Antibodies against neurons (NeuN) are used to evaluate the neuronal transduction capacity in the spinal cord. The spinal cord is also evaluated with an antibody against choline acetlytransferase (ChAT), indicative for motor neurons. Quantification of the total number of neurons expressing EGFP can be performed for spinal cord motor neurons for each animal at each dose using the stereological methods described below.

Absolute numbers of neurons are determined in every fourth section of a series of 40 µm thick brain or 15 µm thick spinal cord using unbiased stereology (optical disector). Systematic sampling of unbiased counting frames can be achieved using a semi-automatic stereology system (Stereo-Investigator, MicroBrightField, Inc.) and a 60×SplanApo oil objective with a numerical aperture of 1.4. Cells that intersect the uppermost focal (exclusion) plane and those that intersect the exclusion boundaries of the unbiased sampling frame are excluded from counting. Cells that meet the counting criteria through a 40 µm or 15 µm axial distance will be counted according to the optical dissector principle. A reference volume is determined by summing the traced areas for each section multiplied by the distance between sections sampled. The mean cell number per disector volume is then multiplied by the reference volume to estimate the total cell numbers.

10. Intermuscular Injections of AAV Containing a Gene Encoding IGF-1 Prolongs Survival in ALS Mice Having the G93A Mutation The following experiments demonstrate that intermuscularly injected AAV containing IGF-1 (AAV-IGF-1) prolongs the survival of mice afflicted with ALS. In these experiments nine ALS mice were examined. ALS mice displayed disease onset symptoms between 87–92 days as assessed by evaluating performance and motor limb movements on the Rotorod test. The nine ALS mice were administered 15 ul bilateral injections of $5 \times 10^{12}$ particles/ml of AAV containing a gene encoding IGF-1 (AAV-IGF-1) into the hindlimb and intercostal muscles at between 85 and 90 days of age. In this experiment, 10 non-injected age- and litter-matched animals were used as controls.

Figure 2:
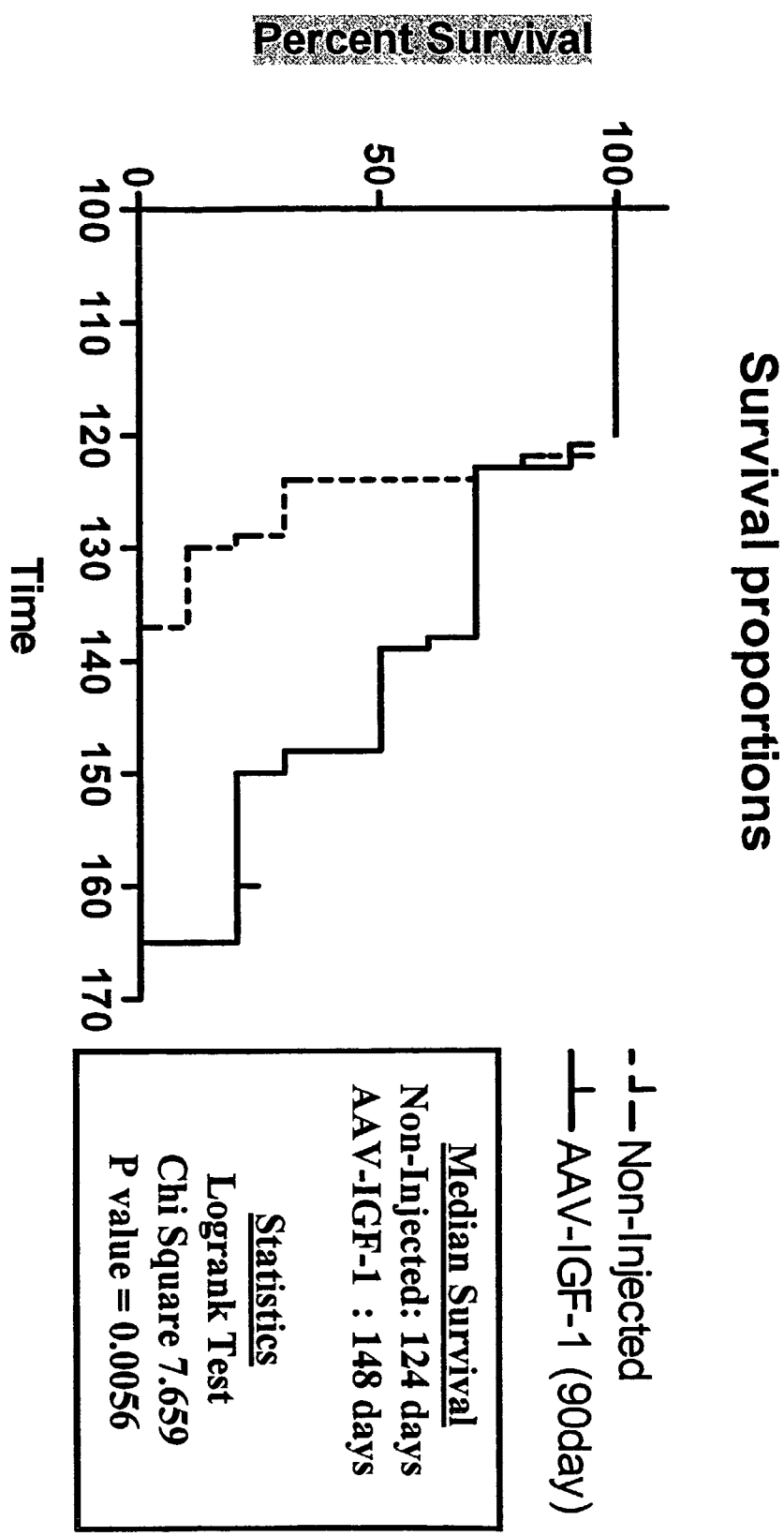
FIG. 2 is a graph which displays a Kaplan-Meyer Survival Curves for both 90 day old ALS-mice intermuscularly injected with AAV-IGF-1 and non-injected mice of the same age.

Mean survival was significantly increased for AAV-IGF-1-treated animals compared to the non-injected animals (FIG. 1). AAV-IGF-1-treated animals as a group survived 24 days longer than non-injected animals, (148 days versus 124 days, respectively). Interestingly, 33% of the animals in the IGF-1 group died by 124 days ('non-responders') compared to 70% of the non-injected animals. Of the surviving IGF-1 animals, their mean survival was 147 days, a 23-day increase in survival compared to the control group (see FIG. 1). No animals in the control group survived past 137 days. The difference between groups is significantly different in the Kaplan-Meyer Survival Curve (Logrank, Chi Square 7.659, p=0.0056) as shown in FIG. 2.

Figure 3:
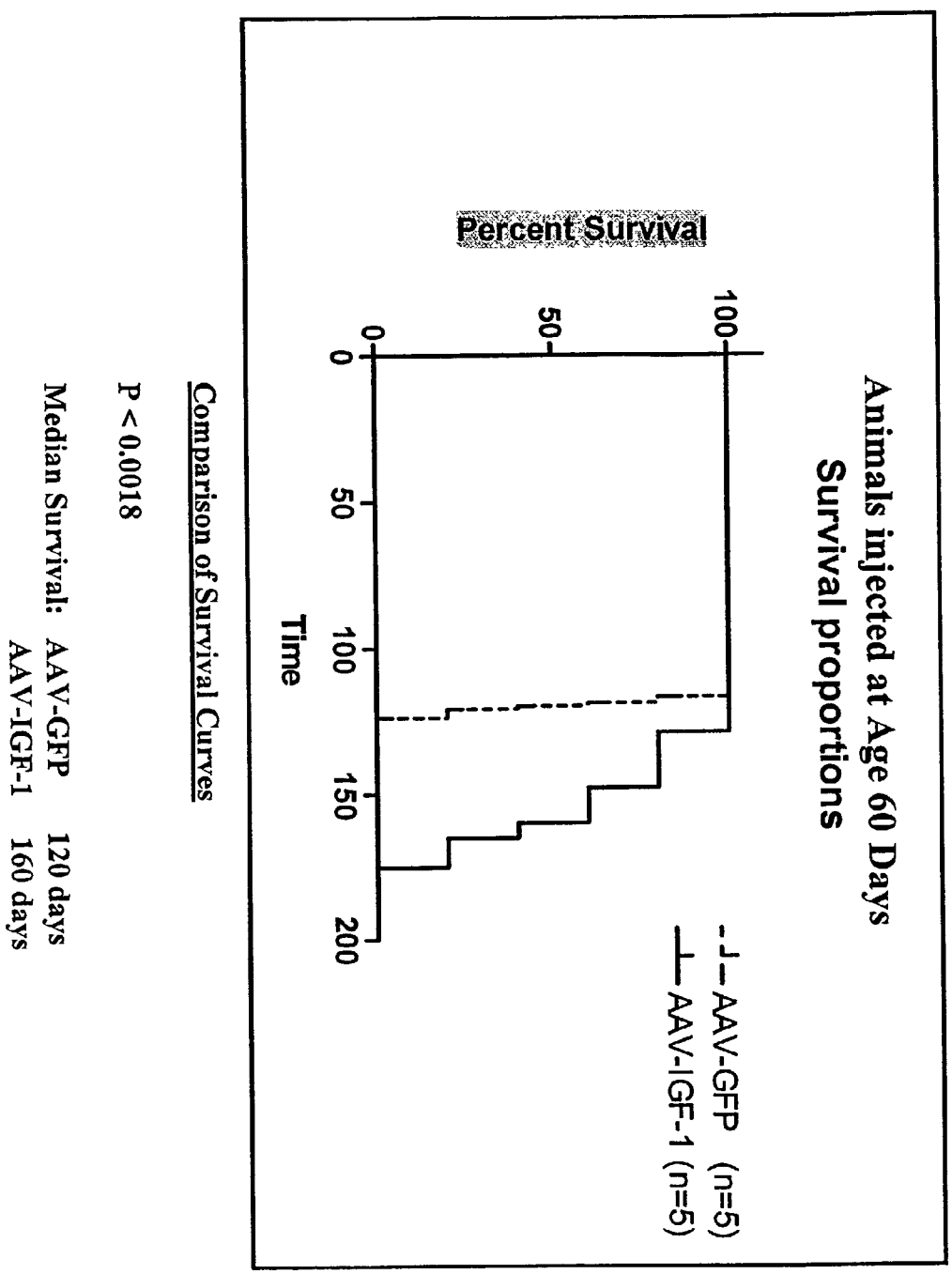
FIG. 3 is a graph which displays a Kaplan-Meyer Survival Curves for both 60 day old ALS-mice intermuscularly injected with AAV-IGF-1 and 60 day old mice intermuscularly injected with AAV-GFP.

The same experiment as described above was also performed using 60 day old mice. FIG. 3 displays a Kaplan-Meyer Survival Curve which shows that the mean survival of mice injected with AAV-IGF-1 at 60 days of age had a median survival of 40 days greater than control mice injected with AAV-GFP.

Because the late injection period at day 90 (the time of disease etiology in G93A animals) more clearly represents the interventional timing in the clinical setting, therapeutic approaches can be aimed at slowing or preventing further disease progression and motor neuron cell death. Such an approach is described in the next Example.

Figure 4:
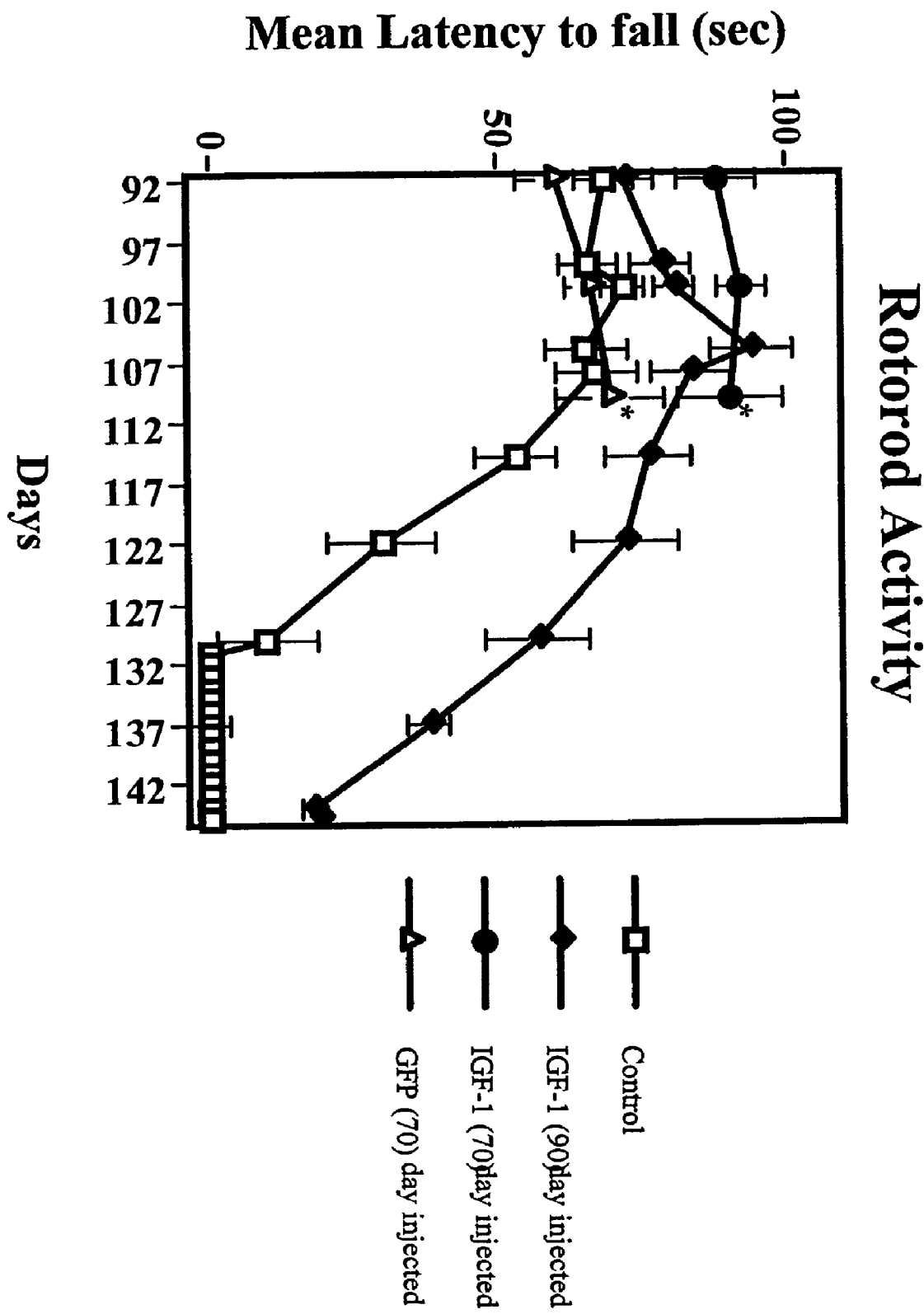
FIG. 4 is a graph which displays mean latency to fall on an accelerating rotorod test for 70 and 90 day old ALS mice intermuscularly injected with AAV-IGF-1 as well as 70 and 90 day old control ALS mice.

11. Intermuscular Injection of AAV-IGF-1 Delays Motor Decline and Disease Progression as Indicated by Increased Performance on the Rotorod Test Expression of IGF-1 in motor neurons significantly delayed the onset of gross motor impairment as assessed by latency to fall on the accelerating Rotorod test. In these experiments, 90 day old ALS mice were given quadracep and intercostal muscle injections of AAV-IGF-1. Non-injected mice of the same age were used as controls. Additionally 70 day old ALS mice were given quadracep and intercostal muscle injection of AAV-IGF-1 or AVV-GFP. Animals treated on day 90 displayed improved performance compared to the corresponding control animals approximately 1 week after injection and continued to improve throughout 2 weeks after injection. Mean latency to fall increased approximately 20 seconds for IGF-1-treated animals (from 72 seconds to 93 seconds). FIG. 4 shows that animals injected with AAV-IGF-1 at 90 days were able to perform the Rotorod behavioral test for an additional 2 weeks compared to control animals (130 versus 144 days). Animals that were injected with AAV-IGF-1 (n=12) at 70 days also displayed increased performance on the Rotorod test compared to AAV-GFP (n=8) animals (FIG. 4).

Figure 5A:
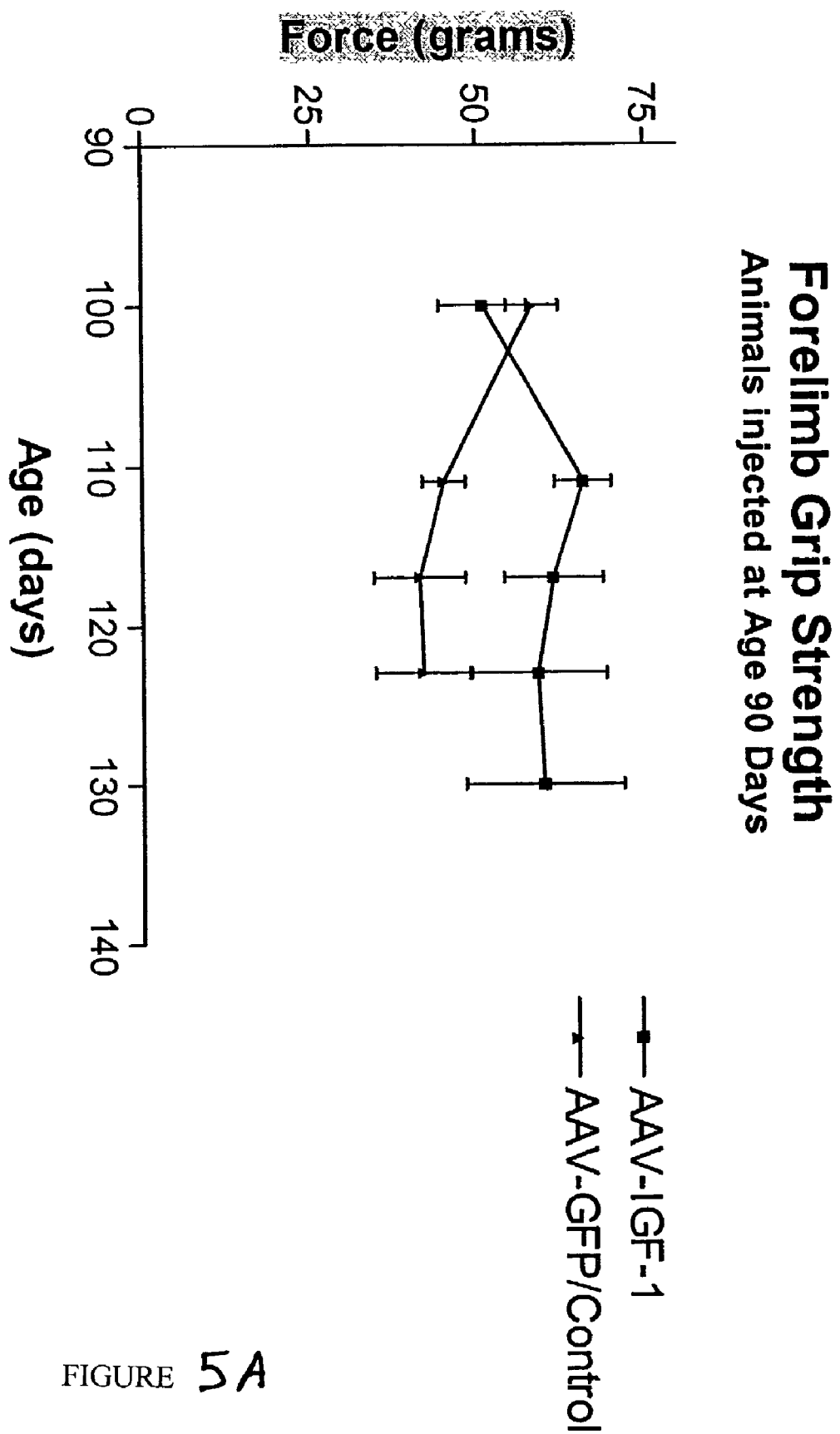
FIGS. 5A–5C are graphs which show the grip strength of 90 day old ALS mice injected with AAV-IGF-1 or AAV-GFP. Forelimb (6A), Hindlimb (6B) and All-limbs (6C).
Figure 5B:
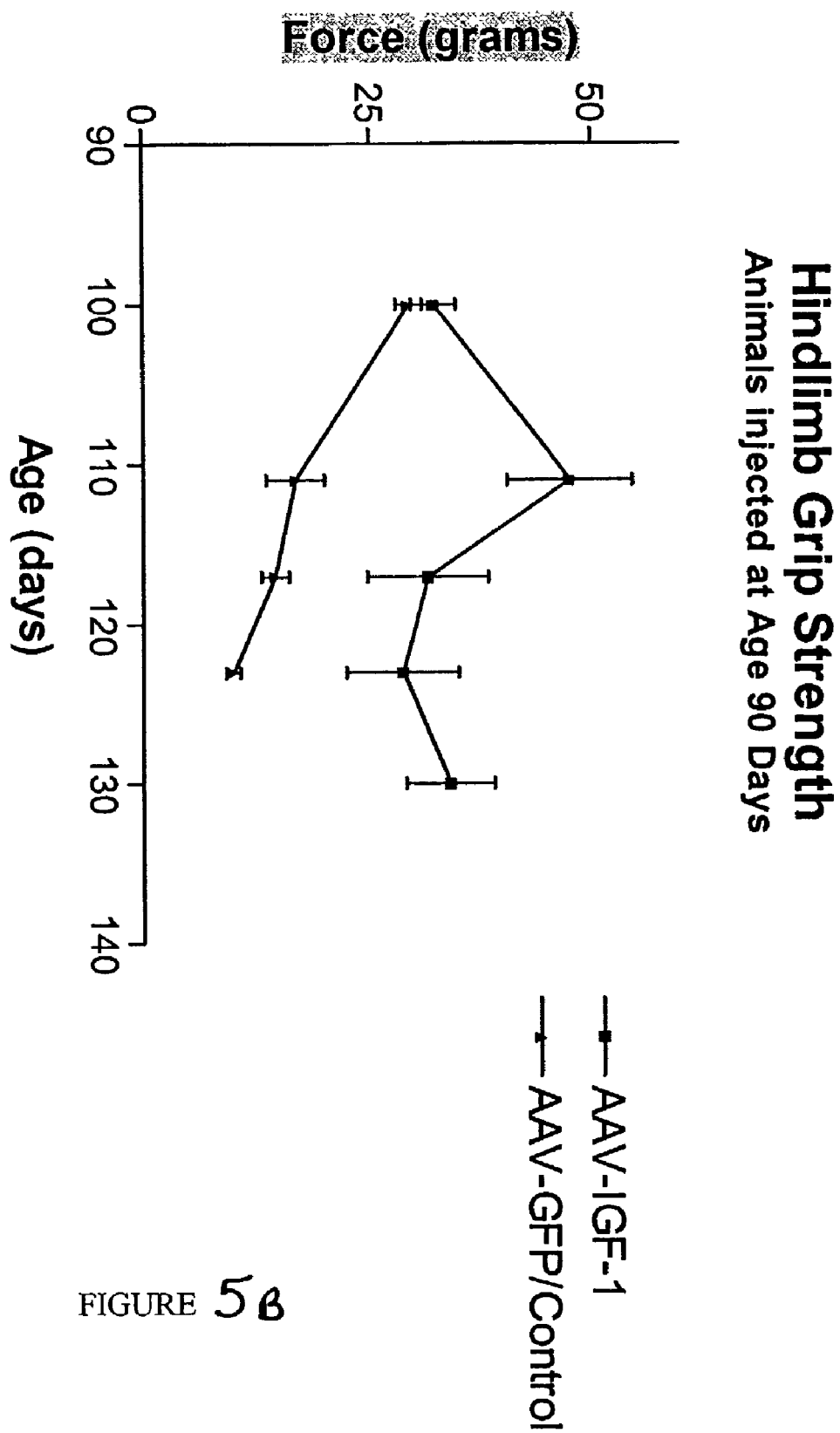
Figure 5C:
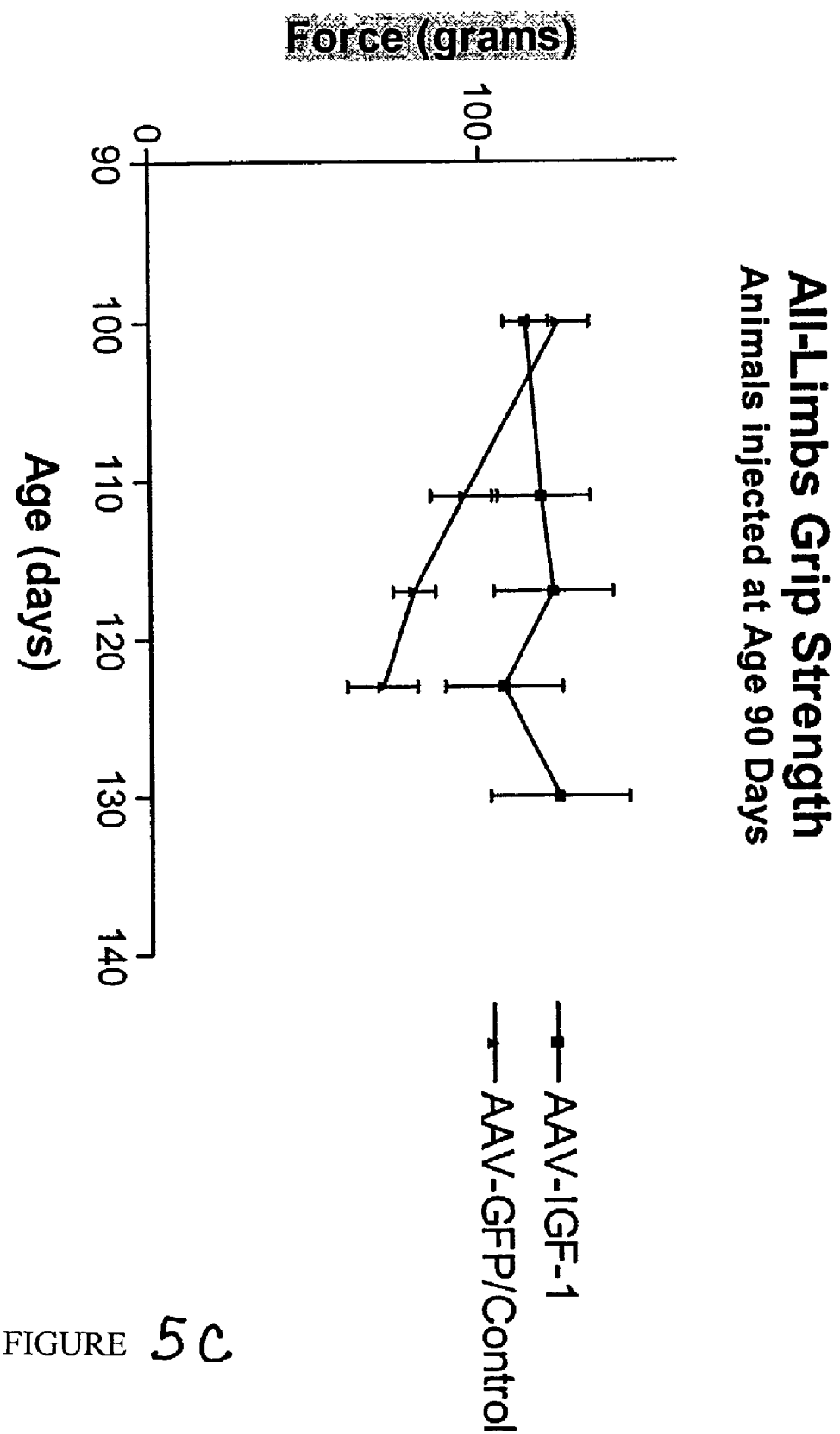

12. Intermuscular Injection of AAV-IGF-1 Delays Motor Decline and Disease Progression as Indicated by Increased Muscle Mass, Stamina and Grip Strength The following experiments demonstrate protection from motor decline in animals treated with AAV-IGF-1 compared to control animals as measured by increased muscle mass, stamina and grip strength. ALS mice were treated as indicated in the previous example. Beginning at 10 days post injection forelimb, hindlimb and all-limb grip strength tests were performed using a grip strength meter (Columbus Instruments). The grip strength meter assesses neuromuscular function by recording the peak amount of force an animal applies in grasping a pull bar platform while being pulled along a straight line leading away from the sensor. The force that is applied to the pull bar is recorded by precision force gauges and peak force is displayed on a digital display. Forelimb and hindlimb gripping strength measurements can be performed independently or together to provide a combined measurement for all-limbs. All animals were tested 4 times each for forelimb, hindlimb, and all-limbs with a 1 minute period of rest between trials. The results of these test are summarized graphically in FIGS. 5A–5C. In each test, AAV-IGF-1-treated mice showed little decrease in grip strength over the 30 day test period whereas control mice showed a significant decrease in grip strength by day 20 of the test period.

Figure 6:
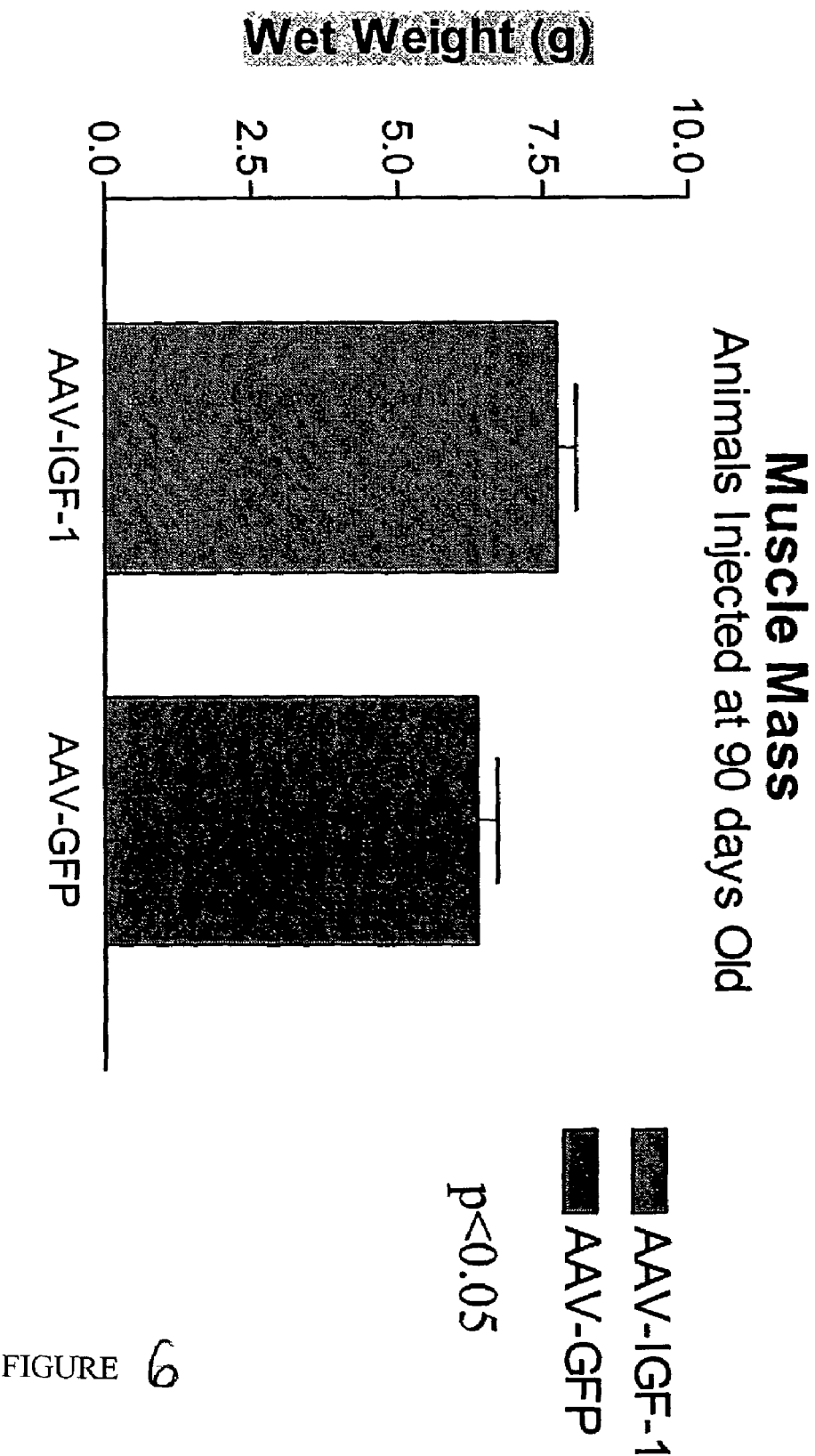
FIG. 6 is a graph showing the increase muscle mass of ALS mice treated with AAV-IGF-1 at 90 days of age compared to the muscle mass of ALS mice treated with AAV-GFP at 90 days of age.

In a second experiment, both AAV-IGF-1 treated mice and control mice were sacrificed at day 25 post injection and the injected muscles were removed and their mass was determined. FIG. 6 shows that the increase in the mean muscle mass for the AAV-IGF-1-treated mice compared to the mean muscle mass for the control mice was statistically significant ($p<0.05$).

In another experiment, the stamina of 90 day old mice injected with AVV-IGF-1 was compared to control mice receiving no injection by measuring the daily running activity of each animal. To obtain these measurements, animals were placed in a running cage and running activity was quantified by the number of revolutions of the running wheel generated by each mouse per day. FIGS. 7B shows that the decrease in running activity of control mice is noticeable, especially starting at about day 105. In contrast, the running activity of AAV-IGF-1 treated mice is similar throughout the duration of the experiment (FIG. 7A).

13. ALS/Spinal Injury in Humans

In addition, as described above, a rAAV vector bearing a therapeutic gene, such as nerve growth factor or insulin-like growth factor I, can be injected into a person at the high titers described above into a muscle innervated by a spinal motor neuron affected by a neurodegenerative disease such as ALS or by a spinal cord injury. Subsequent retrograde transport of the virus can be used to deliver the therapeutic transgenes to the spinal cord. Such methods may be used in treating amyotrophic lateral sclerosis (ALS), spinal motor neuron diseases, and spinal cord injury.

14. Treatment of ALS in Humans

The following example describes a specific method for treating ALS in humans. A sterile preparation of AAV containing an expressible IGF-1 gene is concentrated to $5 \times 10^{10}$ particles/µl in an acceptable carrier. Human subjects diagnosed with ALS are injected with 100 µl doses of the AVV-IGF-1 preparation in the diaphragm according to a daily regimen. The AAV is then retrogradely delivered to the cell body of motor neurons that control breathing. Expression of IGF-1 in these cell bodies increases the respiratory ability of treated ALS patients when compared with the respiratory ability of untreated patients. Other genes encoding proteins useful for treating ALS can likewise be used.

15. Intermuscular Injection of AAV-IGF-1 Produces Secreted Protein

The following experiment describes a method for detecting heterologous proteins secreted by spinal motor neurons that are co-transfected with AAV-GFP and AAV-IGF-1. Intercostal muscle injections AAV-GFP and AAV-IGF-1 are provided to wildtype mice as described above. At daily intervals beginning one day post injection, animals are sacrificed and the spinal cords are removed and evaluated for GFP expression by cryostrat sectioning and histochemistry followed by confocal microscopy. In spinal regions where GFP is present extracellular localization of IGF-1 is detected using labeled antibody specific to IGF-1. The distance of diffusion from the neuronal membrane of bound antibody-labeled IGF-1 is then measured.

Proteins that are not normally secreted can also be monitored by fusing the gene encoding the protein of interest with nucleic acid encoding HIV-TAT secretory sequence. The fusion construct is placed under the control of the CMV promoter in AAV and then co-injected with AAV-GFP into intercostal muscle as described above.

16. Blocking Signaling and Antisense

Furthermore, rAAV vector bearing an antisense gene may be employed in order to inhibit activity in a neuron. Such applications may be of use, for example, in ameliorating calcium toxicity when Ca-binding proteins are overexpressed and lead to the sequestering of calcium in neurons or when antisense vectors against particular receptors, such as glutamate receptors, are used to eliminate or decrease receptor numbers.

Furthermore, the therapeutic methods described above are not limited to the genes described; other genes, such as those encoding FGF proteins, NGF, CNTF, NT-3, neurotrophic factors such as BDNF and GDNF (see, e.g., Yuen E C, Phys Med Rehabil Clin N Am. (2001) 12(2):293–306, viii), or any gene which may be of therapeutic interest when retrogradely transported and expressed, may be employed. This approach could involve, for example, both the delivery of the gene encoding tyrosine hydroxylase to boost dopamine production or the delivery of genes encoding neurotrophic factors such as GDNF to promote the survival of dopaminergic neurons.

Although the foregoing description of the invention has shown, described and pointed out novel features of the invention, it will be understood that various omissions, substitutions, and changes in the form of the detail of the apparatus as illustrated, as well as the uses thereof, may be made by those skilled in the art without departing from the spirit of the present invention. Consequently the scope of the invention should not be limited to the foregoing discussion but should be defined by the following claims.

What is claimed is:

1. A method for delivering a heterologous gene to a cell body of a neuron, comprising:
   contacting a muscle tissue innervated by said neuron with an AAV viral vector comprising a heterologous gene, wherein said AAV viral vector enters said neuron and is retrogradely moved to the cell body.

2. The method of claim 1, wherein said AAV viral vector exhibits tropism toward neurons.

3. The method of claim 1, wherein said neuron is a motor neuron.

4. The method of claim 1, wherein at least $1.5 \times 10^7$ infectious particles of said AAV viral vector are provided.

5. The method of claim 1, wherein at least $1.5 \times 10^8$ infectious particles of said AAV viral vector are provided.

6. The method of claim 1, wherein at least $1.5 \times 10^9$ infectious particles of said AAV viral vector are provided.

7. The method of claim 1, wherein said heterologous gene is stably integrated.

8. The method of claim 1, wherein said gene is expressed.

9. The method of claim 8, wherein said gene is expressed by said neuron for at least two months.

10. The method of claim 8, wherein said gene is expressed by said neuron for at least four months.

11. A method for expressing a protein that is secreted from a target neuron, said method comprising:
    contacting a muscle tissue innervated by said neuron with an AAV viral vector comprising a heterologous gene encoding said protein, wherein said AAV viral vector enters said neuron and is retrogradely moved to the cell body where said gene is expressed.

12. The method of claim 11, wherein the expression of said secreted protein is constitutive.

13. The method of claim 11, wherein the expression of said secreted protein is regulatable.

* * * * *